(12) United States Patent
Tohata et al.

(10) Patent No.: US 8,778,650 B2
(45) Date of Patent: Jul. 15, 2014

(54) ALKALINE PROTEASE VARIANTS

(75) Inventors: Masatoshi Tohata, Haga-gun (JP); Mitsuyoshi Okuda, Haga-gun (JP); Tsuyoshi Sato, Haga-gun (JP); Keiji Endo, Haga-gun (JP); Katsuhisa Saeki, Haga-gun (JP)

(73) Assignee: Kao Corporation, Tokyo (JP)

( * ) Notice: Subject to any disclaimer, the term of this patent is extended or adjusted under 35 U.S.C. 154(b) by 211 days.

(21) Appl. No.: 13/266,525

(22) PCT Filed: Apr. 26, 2010

(86) PCT No.: PCT/JP2010/057838
§ 371 (c)(1),
(2), (4) Date: Oct. 27, 2011

(87) PCT Pub. No.: WO2010/126156
PCT Pub. Date: Nov. 4, 2010

(65) Prior Publication Data
US 2012/0058928 A1    Mar. 8, 2012

(30) Foreign Application Priority Data

| Apr. 30, 2009 | (JP) | 2009-110792 |
| Apr. 30, 2009 | (JP) | 2009-110793 |
| Apr. 14, 2010 | (JP) | 2010-093307 |
| Apr. 14, 2010 | (JP) | 2010-093339 |

(51) Int. Cl.
*C12N 9/54* (2006.01)
*C11D 3/386* (2006.01)

(52) U.S. Cl.
CPC ........ *C11D 3/38618* (2013.01); *C11D 3/38681* (2013.01); *C12N 9/54* (2013.01); *C11D 3/386* (2013.01)
USPC ........................................................ 435/221

(58) Field of Classification Search
None
See application file for complete search history.

(56) References Cited

U.S. PATENT DOCUMENTS

| 5,972,873 | A | 10/1999 | Nielsen et al. |
| 6,376,227 | B1 | 4/2002 | Takaiwa et al. |
| 2002/0064854 | A1 | 5/2002 | Takaiwa et al. |
| 2003/0022351 | A1 | 1/2003 | Hatada et al. |
| 2004/0002343 | A1 | 1/2004 | Brauel et al. |
| 2004/0142837 | A1 | 7/2004 | Takaiwa et al. |
| 2004/0203129 | A1 | 10/2004 | Hatada et al. |
| 2005/0214922 | A1 | 9/2005 | Okuda et al. |
| 2007/0015240 | A1* | 1/2007 | Svendsen et al. ............ 435/69.1 |
| 2008/0177040 | A1 | 7/2008 | Okuda et al. |
| 2008/0187958 | A1 | 8/2008 | Nielsen et al. |
| 2009/0148889 | A1 | 6/2009 | Nielsen et al. |

FOREIGN PATENT DOCUMENTS

| CN | 1113953 A | 12/1995 |
| EP | 0 929 636 B1 | 12/2002 |
| EP | 1 347 044 A2 | 9/2003 |
| WO | WO 2006/032278 A1 | 3/2006 |
| WO | WO 2006/032279 A1 | 3/2006 |

OTHER PUBLICATIONS

GenBank database gi:12381945, from Saeki et al, Novel oxidatively stable subtilisin-like serine proteases from alkaliphilic *Bacillus* spp.: enzymatic properties, sequences, and evolutionary relationships. Biochem. Biophys. Res. Commun. 279 (2), 313-319 (2000). Alignment with Seq ID No. 2.*
Issued_Patents_AA database. Svendsen et al, (20070015240; Jan. 18, 2007) SEQ ID No. 1. Alignment with SEQ ID No. 2 herein.*
Del Mar et al, Substrate specificity of human pancreatic elastase 2. Biochemistry. Feb. 5, 1980;19(3):468-72.*
Notification of First Office Action for Chinese Patent Application No. 201080019156.4, mailed Oct. 10, 2012, Patent Office of the People's Republic of China, Beijing, China.
International Search Report (ISR) for PCT/JP2010/057838, I.A. fd: Apr. 26, 2010, mailed Nov. 10, 2010 from the European Patent Office, Rijswijk, The Netherlands.
International Preliminary report on Patentability (Chapter 1 of the Patent Cooperation Treaty) for PCT/JP2010/057838, I.A. fd: Apr. 26, 2010, issued Nov. 1, 2011, from the International Bureau of WIPO, Geneva, Switzerland.
Saeki, K et al., "Novel oxidatively stable subtilisin-like serine proteases from alkaliphilic *Bacillus* spp.: enzymatic properties, sequences, and evolutionary relationships," Biochem Biophys Res Commun, 279(2):313-319 (Dec. 2000), Academic Press, New York.
Ohta, M. et al., "A dextran-protease conjugate for cosmetic use," Cosmetics & Toiletries magazine 111:79-88 (Jun. 1996), Allured Publishing Corp., Carol Stream, Il.
Crutzen, A et al., "Detergent Enzymes: A Challenge!", Chapter 18 in: Handbook of Detergents, Part A: Properties, G. Broze, ed., pp. 639-690, 1999, Marcel Dekker, New York.
Kobayashi, T et al., "Purification and properties of an alkaline protease from alkalophilic *Bacillus* sp. KSM-K16," Appl Microbiol Biotechnol, Jul. 1995; 43(3): 473-481, Springer Verlag, Berlin, Germany.

* cited by examiner

*Primary Examiner* — Sheridan Swope
(74) *Attorney, Agent, or Firm* — Sterne, Kessler, Goldstein & Fox P.L.L.C.

(57) ABSTRACT

The invention is directed to an alkaline protease that has the amino acid sequence of SEQ ID NO: 2 or of an amino acid sequence having an identity of 90% or more thereto, except that one or more amino acid residues at positions selected from (a) position 6, (b) position 15, (c) position 16, (d) position 65, (e) position 66, (f) position 82, (g) position 83, (h) position 204, (i) position 319, and (j) position 337 of SEQ ID NO: 2, or at positions corresponding thereto, are substituted with certain other amino acid residues. The invention is also directed to detergent compositions and culture medium that contain the protease.

16 Claims, 5 Drawing Sheets

SEQUENCE LISTING

<160> NUMBER OF SEQ ID NOS: 200

<210> SEQ ID NO 1
<211> LENGTH: 2040
<212> TYPE: DNA
<213> ORGANISM: Bacillus sp. KSM-KP43

<400> SEQUENCE: 1

```
ggatccgtga ggagggaacc gaatgagaaa gaagaaaaag gtgttttat ctgttttatc      60
agctgcagcg attttgtcga ctgttgcgtt aagtaatcca tctgcaggtg gtgcaaggaa    120
ttttgatctg gatttcaaag gaattcagac aacaactgat gctaaaggtt tctccaagca    180
ggggcagact ggtgctgctg ctttctggt ggaatctgaa aatgtgaaac tcccaaaagg     240
tttgcagaag aagcttgaaa cagtcccggc aaataataaa ctccatatta tccaattcaa    300
tggaccaatt ttagaagaaa caaaacagca gctggaaaaa cagggcaa agattctcga      360
ctacatacct gattatgctt acattgtcga gtatgagggc gatgttaagt cagcaacaag    420
caccattgag cacgtggaat ccgtggagcc ttatttgccg atatacagaa tagatcccca    480
gcttttcaca aaaggggcat cagagcttgt aaaagcagtg gcgcttgata caaagcagaa    540
aaataaagag gtgcaattaa gaggcatcga acaaatcgca caattcgcaa taagcaatga    600
tgtgctatat attacggcaa agcctgagta taaggtgatg aatgatgttg cgcgtggaat    660
tgtcaaagcg gatgtggctc agagcagcta cgggttgtat ggacaaggac agatcgtagc    720
ggttgccgat acagggcttg atacaggtcg caatgacagt tcgatgcatg aagccttccg    780
cgggaaaatt actgcattat atgcattggg acggacgaat aatgccaatg atacgaatgg    840
tcatggtacg catgtggctg gctccgtatt aggaaacggc tccactaata aggaatggc    900
gcctcaggcg aatctagtct tccaatctat catggatagc ggtgggggac ttggaggact    960
accttcgaat ctgcaaacct tattcagcca agcatacagt gctggtgcca gaattcatac   1020
aaactcctgg ggagcagcag tgaatggggc ttacacaaca gattccagaa atgtggatga   1080
ctatgtgcgc aaaaatgata tgacgatcct tttcgctgcc gggaatgaag gaccgaacgg   1140
cggaaccatc agtgcaccag gcacagctaa aaatgcaata acagtcggag ctacggaaaa   1200
cctccgccca agctttgggt cttatgcgga caatatcaac catgtggcac agttctcttc   1260
acgtggaccg acaaaggatg gacggatcaa accggatgtc atggcaccgg gaacgttcat   1320
actatcagca agatcttctc ttgcaccgga ttcctccttc tgggcgaacc atgacagtaa   1380
atatgcatac atgggtggaa cgtccatggc tacaccgatc gttgctggaa acgtggcaca   1440
gcttcgtgag catttttgtga aaacagagg catcacacca aagccttctc tattaaaagc   1500
ggcactgatt gccggtgcag ctgacatcgg ccttggctac ccgaacggta accaaggatg   1560
gggacgagtg acattggata aatccctgaa cgttgcctat gtgaacgagt ccagttctct   1620
atccaccagc caaaaagcga cgtactcgtt tactgctact gccggcaagc ctttgaaaat   1680
ctccctggta tggtctgatg ccccctgcga g cacaactgct tccgtaacgc ttgtcaatga   1740
tctggacctt gtcattaccg ctccaaatgg cacacagtat gtaggaaatg actttacttc   1800
gccatacaat gataactggg atggccgcaa taacgtagaa aatgtatttta ttaatgcacc   1860
acaaagcggg acgtatacaa ttgaggtaca ggcttataac gtaccggttg gaccacagac   1920
cttctcgttg gcaattgtga attaatagaa taacagacaa aaaacgctgg cgtatgccag   1980
ggttttttttg tttgaaatca agaaaaaagg gtagaggaat taatatggta atcgtctaga   2040
```

<210> SEQ ID NO 2
<211> LENGTH: 434
<212> TYPE: PRT
<213> ORGANISM: Bacillus sp. KSM-KP43

<400> SEQUENCE: 2

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
            50                  55                  60

Thr Asn Gly His Gly Thr His Val Ala Gly Ser Val Leu Gly Asn Gly
65                      70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
            130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
            210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
            275                 280                 285

Leu Ile Ala Gly Ala Ala Asp Ile Gly Leu Gly Tyr Pro Asn Gly Asn
            290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
            355                 360                 365

Asp Leu Val Ile Thr Ala Pro Asn Gly Thr Gln Tyr Val Gly Asn Asp
            370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
```

420         425         430
Val Asn

<210> SEQ ID NO 3
<211> LENGTH: 26
<212> TYPE: DNA
<213> ORGANISM: Artificial
<220> FEATURE:
<223> OTHER INFORMATION: Oligonucleotide as PCR primer KG24S2

<400> SEQUENCE: 3
ataaggatcc gtgaggaggg aaccga                                          26

<210> SEQ ID NO 4
<211> LENGTH: 21
<212> TYPE: DNA
<213> ORGANISM: Artificial
<220> FEATURE:
<223> OTHER INFORMATION: Oligonucleotide as PCR primer G6_R

<400> SEQUENCE: 4
acgcgcaaca tcattcatca c                                               21

<210> SEQ ID NO 5
<211> LENGTH: 45
<212> TYPE: DNA
<213> ORGANISM: Artificial
<220> FEATURE:
<223> OTHER INFORMATION: Oligonucleotide as PCR primer G6A_F

<400> SEQUENCE: 5
gtgatgaatg atgttgcgcg tgcaattgtc aaagcggatg tggct                     45

<210> SEQ ID NO 6
<211> LENGTH: 36
<212> TYPE: DNA
<213> ORGANISM: Artificial
<220> FEATURE:
<223> OTHER INFORMATION: Oligonucleotide as PCR primer KG11S

<400> SEQUENCE: 6
cccctctaga cgattaccat attaattcct ctaccc                               36

<210> SEQ ID NO 7
<211> LENGTH: 45
<212> TYPE: DNA
<213> ORGANISM: Artificial
<220> FEATURE:
<223> OTHER INFORMATION: Oligonucleotide as PCR primer G6C_F

<400> SEQUENCE: 7
gtgatgaatg atgttgcgcg ttgcattgtc aaagcggatg tggct                     45

<210> SEQ ID NO 8
<211> LENGTH: 45
<212> TYPE: DNA
<213> ORGANISM: Artificial
<220> FEATURE:
<223> OTHER INFORMATION: Oligonucleotide as PCR primer G6D_F

<400> SEQUENCE: 8
gtgatgaatg atgttgcgcg tgatattgtc aaagcggatg tggct                     45

<210> SEQ ID NO 9
<211> LENGTH: 45

-continued

```
<212> TYPE: DNA
<213> ORGANISM: Artificial
<220> FEATURE:
<223> OTHER INFORMATION: Oligonucleotide as PCR primer G6E_F

<400> SEQUENCE: 9
gtgatgaatg atgttgcgcg tgaaattgtc aaagcggatg tggct              45

<210> SEQ ID NO 10
<211> LENGTH: 45
<212> TYPE: DNA
<213> ORGANISM: Artificial
<220> FEATURE:
<223> OTHER INFORMATION: Oligonucleotide as PCR primer G6F_F

<400> SEQUENCE: 10
gtgatgaatg atgttgcgcg tttcattgtc aaagcggatg tggct              45

<210> SEQ ID NO 11
<211> LENGTH: 45
<212> TYPE: DNA
<213> ORGANISM: Artificial
<220> FEATURE:
<223> OTHER INFORMATION: Oligonucleotide as PCR primer G6H_F

<400> SEQUENCE: 11
gtgatgaatg atgttgcgcg tcatattgtc aaagcggatg tggct              45

<210> SEQ ID NO 12
<211> LENGTH: 45
<212> TYPE: DNA
<213> ORGANISM: Artificial
<220> FEATURE:
<223> OTHER INFORMATION: Oligonucleotide as PCR primer G6I_F

<400> SEQUENCE: 12
gtgatgaatg atgttgcgcg tattattgtc aaagcggatg tggct              45

<210> SEQ ID NO 13
<211> LENGTH: 45
<212> TYPE: DNA
<213> ORGANISM: Artificial
<220> FEATURE:
<223> OTHER INFORMATION: Oligonucleotide as PCR primer G6K_F

<400> SEQUENCE: 13
gtgatgaatg atgttgcgcg taaaattgtc aaagcggatg tggct              45

<210> SEQ ID NO 14
<211> LENGTH: 45
<212> TYPE: DNA
<213> ORGANISM: Artificial
<220> FEATURE:
<223> OTHER INFORMATION: Oligonucleotide as PCR primer G6L_F

<400> SEQUENCE: 14
gtgatgaatg atgttgcgcg tcttattgtc aaagcggatg tggct              45

<210> SEQ ID NO 15
<211> LENGTH: 45
<212> TYPE: DNA
<213> ORGANISM: Artificial
<220> FEATURE:
<223> OTHER INFORMATION: Oligonucleotide as PCR primer G6M_F

<400> SEQUENCE: 15
```
gtgatgaatg atgttgcgcg tatgattgtc aaagcggatg tggct        45

<210> SEQ ID NO 16
<211> LENGTH: 45
<212> TYPE: DNA
<213> ORGANISM: Artificial
<220> FEATURE:
<223> OTHER INFORMATION: Oligonucleotide as PCR primer G6N_F

<400> SEQUENCE: 16
gtgatgaatg atgttgcgcg taatattgtc aaagcggatg tggct        45

<210> SEQ ID NO 17
<211> LENGTH: 45
<212> TYPE: DNA
<213> ORGANISM: Artificial
<220> FEATURE:
<223> OTHER INFORMATION: Oligonucleotide as PCR primer G6P_F

<400> SEQUENCE: 17
gtgatgaatg atgttgcgcg tccaattgtc aaagcggatg tggct        45

<210> SEQ ID NO 18
<211> LENGTH: 45
<212> TYPE: DNA
<213> ORGANISM: Artificial
<220> FEATURE:
<223> OTHER INFORMATION: Oligonucleotide as PCR primer G6Q_F

<400> SEQUENCE: 18
gtgatgaatg atgttgcgcg tcagattgtc aaagcggatg tggct        45

<210> SEQ ID NO 19
<211> LENGTH: 45
<212> TYPE: DNA
<213> ORGANISM: Artificial
<220> FEATURE:
<223> OTHER INFORMATION: Oligonucleotide as PCR primer G6R_F

<400> SEQUENCE: 19
gtgatgaatg atgttgcgcg tagaattgtc aaagcggatg tggct        45

<210> SEQ ID NO 20
<211> LENGTH: 45
<212> TYPE: DNA
<213> ORGANISM: Artificial
<220> FEATURE:
<223> OTHER INFORMATION: Oligonucleotide as PCR primer G6S_F

<400> SEQUENCE: 20
gtgatgaatg atgttgcgcg ttccattgtc aaagcggatg tggct        45

<210> SEQ ID NO 21
<211> LENGTH: 45
<212> TYPE: DNA
<213> ORGANISM: Artificial
<220> FEATURE:
<223> OTHER INFORMATION: Oligonucleotide as PCR primer G6T_F

<400> SEQUENCE: 21
gtgatgaatg atgttgcgcg tacaattgtc aaagcggatg tggct        45

<210> SEQ ID NO 22
<211> LENGTH: 45
<212> TYPE: DNA
<213> ORGANISM: Artificial

-continued

```
<220> FEATURE:
<223> OTHER INFORMATION: Oligonucleotide as PCR primer G6V_F

<400> SEQUENCE: 22
gtgatgaatg atgttgcgcg tgtgattgtc aaagcggatg tggct          45

<210> SEQ ID NO 23
<211> LENGTH: 45
<212> TYPE: DNA
<213> ORGANISM: Artificial
<220> FEATURE:
<223> OTHER INFORMATION: Oligonucleotide as PCR primer G6W_F

<400> SEQUENCE: 23
gtgatgaatg atgttgcgcg ttggattgtc aaagcggatg tggct          45

<210> SEQ ID NO 24
<211> LENGTH: 45
<212> TYPE: DNA
<213> ORGANISM: Artificial
<220> FEATURE:
<223> OTHER INFORMATION: Oligonucleotide as PCR primer G6Y_F

<400> SEQUENCE: 24
gtgatgaatg atgttgcgcg ttatattgtc aaagcggatg tggct          45

<210> SEQ ID NO 25
<211> LENGTH: 21
<212> TYPE: DNA
<213> ORGANISM: Artificial
<220> FEATURE:
<223> OTHER INFORMATION: Oligonucleotide as PCR primer S15_R

<400> SEQUENCE: 25
ctgagccaca tccgctttga c                                    21

<210> SEQ ID NO 26
<211> LENGTH: 45
<212> TYPE: DNA
<213> ORGANISM: Artificial
<220> FEATURE:
<223> OTHER INFORMATION: Oligonucleotide as PCR primer S15A_F

<400> SEQUENCE: 26
gtcaaagcgg atgtggctca ggcaagctac gggttgtatg gacaa          45

<210> SEQ ID NO 27
<211> LENGTH: 45
<212> TYPE: DNA
<213> ORGANISM: Artificial
<220> FEATURE:
<223> OTHER INFORMATION: Oligonucleotide as PCR primer S15C_F

<400> SEQUENCE: 27
gtcaaagcgg atgtggctca gtgcagctac gggttgtatg gacaa          45

<210> SEQ ID NO 28
<211> LENGTH: 45
<212> TYPE: DNA
<213> ORGANISM: Artificial
<220> FEATURE:
<223> OTHER INFORMATION: Oligonucleotide as PCR primer S15D_F

<400> SEQUENCE: 28
gtcaaagcgg atgtggctca ggatagctac gggttgtatg gacaa          45
```

<210> SEQ ID NO 29
<211> LENGTH: 45
<212> TYPE: DNA
<213> ORGANISM: Artificial
<220> FEATURE:
<223> OTHER INFORMATION: Oligonucleotide as PCR primer S15E_F

<400> SEQUENCE: 29
gtcaaagcgg atgtggctca ggaaagctac gggttgtatg gacaa          45

<210> SEQ ID NO 30
<211> LENGTH: 45
<212> TYPE: DNA
<213> ORGANISM: Artificial
<220> FEATURE:
<223> OTHER INFORMATION: Oligonucleotide as PCR primer S15F_F

<400> SEQUENCE: 30
gtcaaagcgg atgtggctca gttcagctac gggttgtatg gacaa          45

<210> SEQ ID NO 31
<211> LENGTH: 45
<212> TYPE: DNA
<213> ORGANISM: Artificial
<220> FEATURE:
<223> OTHER INFORMATION: Oligonucleotide as PCR primer S15G_F

<400> SEQUENCE: 31
gtcaaagcgg atgtggctca gggaagctac gggttgtatg gacaa          45

<210> SEQ ID NO 32
<211> LENGTH: 45
<212> TYPE: DNA
<213> ORGANISM: Artificial
<220> FEATURE:
<223> OTHER INFORMATION: Oligonucleotide as PCR primer S15I_F

<400> SEQUENCE: 32
gtcaaagcgg atgtggctca gattagctac gggttgtatg gacaa          45

<210> SEQ ID NO 33
<211> LENGTH: 45
<212> TYPE: DNA
<213> ORGANISM: Artificial
<220> FEATURE:
<223> OTHER INFORMATION: Oligonucleotide as PCR primer S15K_F

<400> SEQUENCE: 33
gtcaaagcgg atgtggctca gaaaagctac gggttgtatg gacaa          45

<210> SEQ ID NO 34
<211> LENGTH: 45
<212> TYPE: DNA
<213> ORGANISM: Artificial
<220> FEATURE:
<223> OTHER INFORMATION: Oligonucleotide as PCR primer S15L_F

<400> SEQUENCE: 34
gtcaaagcgg atgtggctca gcttagctac gggttgtatg gacaa          45

<210> SEQ ID NO 35
<211> LENGTH: 45
<212> TYPE: DNA
<213> ORGANISM: Artificial
<220> FEATURE:
<223> OTHER INFORMATION: Oligonucleotide as PCR primer S15M_F

<400> SEQUENCE: 35
gtcaaagcgg atgtggctca gatgagctac gggttgtatg gacaa                45

<210> SEQ ID NO 36
<211> LENGTH: 45
<212> TYPE: DNA
<213> ORGANISM: Artificial
<220> FEATURE:
<223> OTHER INFORMATION: Oligonucleotide as PCR primer S15N_F

<400> SEQUENCE: 36
gtcaaagcgg atgtggctca gaatagctac gggttgtatg gacaa                45

<210> SEQ ID NO 37
<211> LENGTH: 45
<212> TYPE: DNA
<213> ORGANISM: Artificial
<220> FEATURE:
<223> OTHER INFORMATION: Oligonucleotide as PCR primer S15P_F

<400> SEQUENCE: 37
gtcaaagcgg atgtggctca gccaagctac gggttgtatg gacaa                45

<210> SEQ ID NO 38
<211> LENGTH: 45
<212> TYPE: DNA
<213> ORGANISM: Artificial
<220> FEATURE:
<223> OTHER INFORMATION: Oligonucleotide as PCR primer S15Q_F

<400> SEQUENCE: 38
gtcaaagcgg atgtggctca gcagagctac gggttgtatg gacaa                45

<210> SEQ ID NO 39
<211> LENGTH: 45
<212> TYPE: DNA
<213> ORGANISM: Artificial
<220> FEATURE:
<223> OTHER INFORMATION: Oligonucleotide as PCR primer S15R_F

<400> SEQUENCE: 39
gtcaaagcgg atgtggctca gagaagctac gggttgtatg gacaa                45

<210> SEQ ID NO 40
<211> LENGTH: 45
<212> TYPE: DNA
<213> ORGANISM: Artificial
<220> FEATURE:
<223> OTHER INFORMATION: Oligonucleotide as PCR primer S15T_F

<400> SEQUENCE: 40
gtcaaagcgg atgtggctca gacaagctac gggttgtatg gacaa                45

<210> SEQ ID NO 41
<211> LENGTH: 45
<212> TYPE: DNA
<213> ORGANISM: Artificial
<220> FEATURE:
<223> OTHER INFORMATION: Oligonucleotide as PCR primer S15V_F

<400> SEQUENCE: 41
gtcaaagcgg atgtggctca ggtgagctac gggttgtatg gacaa                45

<210> SEQ ID NO 42

<210> SEQ ID NO 42
<211> LENGTH: 45
<212> TYPE: DNA
<213> ORGANISM: Artificial
<220> FEATURE:
<223> OTHER INFORMATION: Oligonucleotide as PCR primer S15W_F

<400> SEQUENCE: 42
gtcaaagcgg atgtggctca gtggagctac gggttgtatg gacaa          45

<210> SEQ ID NO 43
<211> LENGTH: 45
<212> TYPE: DNA
<213> ORGANISM: Artificial
<220> FEATURE:
<223> OTHER INFORMATION: Oligonucleotide as PCR primer S15Y_F

<400> SEQUENCE: 43
gtcaaagcgg atgtggctca gtatagctac gggttgtatg gacaa          45

<210> SEQ ID NO 44
<211> LENGTH: 21
<212> TYPE: DNA
<213> ORGANISM: Artificial
<220> FEATURE:
<223> OTHER INFORMATION: Oligonucleotide as PCR primer S16_R

<400> SEQUENCE: 44
gctctgagcc acatccgctt t                                    21

<210> SEQ ID NO 45
<211> LENGTH: 45
<212> TYPE: DNA
<213> ORGANISM: Artificial
<220> FEATURE:
<223> OTHER INFORMATION: Oligonucleotide as PCR primer S16A_F

<400> SEQUENCE: 45
aaagcggatg tggctcagag cgcatacggg ttgtatggac aagga          45

<210> SEQ ID NO 46
<211> LENGTH: 45
<212> TYPE: DNA
<213> ORGANISM: Artificial
<220> FEATURE:
<223> OTHER INFORMATION: Oligonucleotide as PCR primer S16C_F

<400> SEQUENCE: 46
aaagcggatg tggctcagag ctgctacggg ttgtatggac aagga          45

<210> SEQ ID NO 47
<211> LENGTH: 45
<212> TYPE: DNA
<213> ORGANISM: Artificial
<220> FEATURE:
<223> OTHER INFORMATION: Oligonucleotide as PCR primer S16D_F

<400> SEQUENCE: 47
aaagcggatg tggctcagag cgattacggg ttgtatggac aagga          45

<210> SEQ ID NO 48
<211> LENGTH: 45
<212> TYPE: DNA
<213> ORGANISM: Artificial
<220> FEATURE:
<223> OTHER INFORMATION: Oligonucleotide as PCR primer S16E_F

<400> SEQUENCE: 48
aaagcggatg tggctcagag cgaatacggg ttgtatggac aagga        45

<210> SEQ ID NO 49
<211> LENGTH: 45
<212> TYPE: DNA
<213> ORGANISM: Artificial
<220> FEATURE:
<223> OTHER INFORMATION: Oligonucleotide as PCR primer S16F_F

<400> SEQUENCE: 49
aaagcggatg tggctcagag cttctacggg ttgtatggac aagga        45

<210> SEQ ID NO 50
<211> LENGTH: 45
<212> TYPE: DNA
<213> ORGANISM: Artificial
<220> FEATURE:
<223> OTHER INFORMATION: Oligonucleotide as PCR primer S16G_F

<400> SEQUENCE: 50
aaagcggatg tggctcagag cggatacggg ttgtatggac aagga        45

<210> SEQ ID NO 51
<211> LENGTH: 45
<212> TYPE: DNA
<213> ORGANISM: Artificial
<220> FEATURE:
<223> OTHER INFORMATION: Oligonucleotide as PCR primer S16H_F

<400> SEQUENCE: 51
aaagcggatg tggctcagag ccattacggg ttgtatggac aagga        45

<210> SEQ ID NO 52
<211> LENGTH: 45
<212> TYPE: DNA
<213> ORGANISM: Artificial
<220> FEATURE:
<223> OTHER INFORMATION: Oligonucleotide as PCR primer S16I_F

<400> SEQUENCE: 52
aaagcggatg tggctcagag catttacggg ttgtatggac aagga        45

<210> SEQ ID NO 53
<211> LENGTH: 45
<212> TYPE: DNA
<213> ORGANISM: Artificial
<220> FEATURE:
<223> OTHER INFORMATION: Oligonucleotide as PCR primer S16K_F

<400> SEQUENCE: 53
aaagcggatg tggctcagag caaatacggg ttgtatggac aagga        45

<210> SEQ ID NO 54
<211> LENGTH: 45
<212> TYPE: DNA
<213> ORGANISM: Artificial
<220> FEATURE:
<223> OTHER INFORMATION: Oligonucleotide as PCR primer S16L_F

<400> SEQUENCE: 54
aaagcggatg tggctcagag cctttacggg ttgtatggac aagga        45

<210> SEQ ID NO 55
<211> LENGTH: 45
<212> TYPE: DNA

<213> ORGANISM: Artificial
<220> FEATURE:
<223> OTHER INFORMATION: Oligonucleotide as PCR primer S16M_F

<400> SEQUENCE: 55
aaagcggatg tggctcagag catgtacggg ttgtatggac aagga        45

<210> SEQ ID NO 56
<211> LENGTH: 45
<212> TYPE: DNA
<213> ORGANISM: Artificial
<220> FEATURE:
<223> OTHER INFORMATION: Oligonucleotide as PCR primer S16N_F

<400> SEQUENCE: 56
aaagcggatg tggctcagag caattacggg ttgtatggac aagga        45

<210> SEQ ID NO 57
<211> LENGTH: 45
<212> TYPE: DNA
<213> ORGANISM: Artificial
<220> FEATURE:
<223> OTHER INFORMATION: Oligonucleotide as PCR primer S16P_F

<400> SEQUENCE: 57
aaagcggatg tggctcagag cccatacggg ttgtatggac aagga        45

<210> SEQ ID NO 58
<211> LENGTH: 45
<212> TYPE: DNA
<213> ORGANISM: Artificial
<220> FEATURE:
<223> OTHER INFORMATION: Oligonucleotide as PCR primer S16R_F

<400> SEQUENCE: 58
aaagcggatg tggctcagag cagatacggg ttgtatggac aagga        45

<210> SEQ ID NO 59
<211> LENGTH: 45
<212> TYPE: DNA
<213> ORGANISM: Artificial
<220> FEATURE:
<223> OTHER INFORMATION: Oligonucleotide as PCR primer S16V_F

<400> SEQUENCE: 59
aaagcggatg tggctcagag cgtgtacggg ttgtatggac aagga        45

<210> SEQ ID NO 60
<211> LENGTH: 45
<212> TYPE: DNA
<213> ORGANISM: Artificial
<220> FEATURE:
<223> OTHER INFORMATION: Oligonucleotide as PCR primer S16W_F

<400> SEQUENCE: 60
aaagcggatg tggctcagag ctggtacggg ttgtatggac aagga        45

<210> SEQ ID NO 61
<211> LENGTH: 45
<212> TYPE: DNA
<213> ORGANISM: Artificial
<220> FEATURE:
<223> OTHER INFORMATION: Oligonucleotide as PCR primer S16Y_F

<400> SEQUENCE: 61
aaagcggatg tggctcagag ctattacggg ttgtatggac aagga        45

<210> SEQ ID NO 62
<211> LENGTH: 21
<212> TYPE: DNA
<213> ORGANISM: Artificial
<220> FEATURE:
<223> OTHER INFORMATION: Oligonucleotide as PCR primer T65_R

<400> SEQUENCE: 62
atcattggca ttattcgtcc g                                              21

<210> SEQ ID NO 63
<211> LENGTH: 45
<212> TYPE: DNA
<213> ORGANISM: Artificial
<220> FEATURE:
<223> OTHER INFORMATION: Oligonucleotide as PCR primer T65A_F

<400> SEQUENCE: 63
cggacgaata atgccaatga tgcaaatggt catggtacgc atgtg                    45

<210> SEQ ID NO 64
<211> LENGTH: 45
<212> TYPE: DNA
<213> ORGANISM: Artificial
<220> FEATURE:
<223> OTHER INFORMATION: Oligonucleotide as PCR primer T65C_F

<400> SEQUENCE: 64
cggacgaata atgccaatga ttgcaatggt catggtacgc atgtg                    45

<210> SEQ ID NO 65
<211> LENGTH: 45
<212> TYPE: DNA
<213> ORGANISM: Artificial
<220> FEATURE:
<223> OTHER INFORMATION: Oligonucleotide as PCR primer T65D_F

<400> SEQUENCE: 65
cggacgaata atgccaatga tgataatggt catggtacgc atgtg                    45

<210> SEQ ID NO 66
<211> LENGTH: 45
<212> TYPE: DNA
<213> ORGANISM: Artificial
<220> FEATURE:
<223> OTHER INFORMATION: Oligonucleotide as PCR primer T65E_F

<400> SEQUENCE: 66
cggacgaata atgccaatga tgaaaatggt catggtacgc atgtg                    45

<210> SEQ ID NO 67
<211> LENGTH: 45
<212> TYPE: DNA
<213> ORGANISM: Artificial
<220> FEATURE:
<223> OTHER INFORMATION: Oligonucleotide as PCR primer T65F_F

<400> SEQUENCE: 67
cggacgaata atgccaatga tttcaatggt catggtacgc atgtg                    45

<210> SEQ ID NO 68
<211> LENGTH: 45
<212> TYPE: DNA
<213> ORGANISM: Artificial
<220> FEATURE:

<223> OTHER INFORMATION: Oligonucleotide as PCR primer T65G_F

<400> SEQUENCE: 68
cggacgaata atgccaatga tggaaatggt catggtacgc atgtg    45

<210> SEQ ID NO 69
<211> LENGTH: 45
<212> TYPE: DNA
<213> ORGANISM: Artificial
<220> FEATURE:
<223> OTHER INFORMATION: Oligonucleotide as PCR primer T65H_F

<400> SEQUENCE: 69
cggacgaata atgccaatga tcataatggt catggtacgc atgtg    45

<210> SEQ ID NO 70
<211> LENGTH: 45
<212> TYPE: DNA
<213> ORGANISM: Artificial
<220> FEATURE:
<223> OTHER INFORMATION: Oligonucleotide as PCR primer T65I_F

<400> SEQUENCE: 70
cggacgaata atgccaatga tattaatggt catggtacgc atgtg    45

<210> SEQ ID NO 71
<211> LENGTH: 45
<212> TYPE: DNA
<213> ORGANISM: Artificial
<220> FEATURE:
<223> OTHER INFORMATION: Oligonucleotide as PCR primer T65K_F

<400> SEQUENCE: 71
cggacgaata atgccaatga taaaaatggt catggtacgc atgtg    45

<210> SEQ ID NO 72
<211> LENGTH: 45
<212> TYPE: DNA
<213> ORGANISM: Artificial
<220> FEATURE:
<223> OTHER INFORMATION: Oligonucleotide as PCR primer T65L_F

<400> SEQUENCE: 72
cggacgaata atgccaatga tcttaatggt catggtacgc atgtg    45

<210> SEQ ID NO 73
<211> LENGTH: 45
<212> TYPE: DNA
<213> ORGANISM: Artificial
<220> FEATURE:
<223> OTHER INFORMATION: Oligonucleotide as PCR primer T65M_F

<400> SEQUENCE: 73
cggacgaata atgccaatga tatgaatggt catggtacgc atgtg    45

<210> SEQ ID NO 74
<211> LENGTH: 45
<212> TYPE: DNA
<213> ORGANISM: Artificial
<220> FEATURE:
<223> OTHER INFORMATION: Oligonucleotide as PCR primer T65N_F

<400> SEQUENCE: 74
cggacgaata atgccaatga taataatggt catggtacgc atgtg    45

<210> SEQ ID NO 75
<211> LENGTH: 45
<212> TYPE: DNA
<213> ORGANISM: Artificial
<220> FEATURE:
<223> OTHER INFORMATION: Oligonucleotide as PCR primer T65Q_F

<400> SEQUENCE: 75
cggacgaata atgccaatga tcagaatggt catggtacgc atgtg          45

<210> SEQ ID NO 76
<211> LENGTH: 45
<212> TYPE: DNA
<213> ORGANISM: Artificial
<220> FEATURE:
<223> OTHER INFORMATION: Oligonucleotide as PCR primer T65R_F

<400> SEQUENCE: 76
cggacgaata atgccaatga tagaaatggt catggtacgc atgtg           45

<210> SEQ ID NO 77
<211> LENGTH: 45
<212> TYPE: DNA
<213> ORGANISM: Artificial
<220> FEATURE:
<223> OTHER INFORMATION: Oligonucleotide as PCR primer T65S_F

<400> SEQUENCE: 77
cggacgaata atgccaatga ttccaatggt catggtacgc atgtg           45

<210> SEQ ID NO 78
<211> LENGTH: 45
<212> TYPE: DNA
<213> ORGANISM: Artificial
<220> FEATURE:
<223> OTHER INFORMATION: Oligonucleotide as PCR primer T65V_F

<400> SEQUENCE: 78
cggacgaata atgccaatga tgtgaatggt catggtacgc atgtg           45

<210> SEQ ID NO 79
<211> LENGTH: 45
<212> TYPE: DNA
<213> ORGANISM: Artificial
<220> FEATURE:
<223> OTHER INFORMATION: Oligonucleotide as PCR primer T65W_F

<400> SEQUENCE: 79
cggacgaata atgccaatga ttggaatggt catggtacgc atgtg           45

<210> SEQ ID NO 80
<211> LENGTH: 45
<212> TYPE: DNA
<213> ORGANISM: Artificial
<220> FEATURE:
<223> OTHER INFORMATION: Oligonucleotide as PCR primer T65Y_F

<400> SEQUENCE: 80
cggacgaata atgccaatga ttataatggt catggtacgc atgtg           45

<210> SEQ ID NO 81
<211> LENGTH: 21
<212> TYPE: DNA
<213> ORGANISM: Artificial
<220> FEATURE:
<223> OTHER INFORMATION: Oligonucleotide as PCR primer N66_R

<400> SEQUENCE: 81
cgtatcattg gcattattcg t　　　　　　　　　　　　　　　　　　　　　21

<210> SEQ ID NO 82
<211> LENGTH: 45
<212> TYPE: DNA
<213> ORGANISM: Artificial
<220> FEATURE:
<223> OTHER INFORMATION: Oligonucleotide as PCR primer N66A_F

<400> SEQUENCE: 82
acgaataatg ccaatgatac ggcaggtcat ggtacgcatg tggct　　　　　　　45

<210> SEQ ID NO 83
<211> LENGTH: 45
<212> TYPE: DNA
<213> ORGANISM: Artificial
<220> FEATURE:
<223> OTHER INFORMATION: Oligonucleotide as PCR primer N66C_F

<400> SEQUENCE: 83
acgaataatg ccaatgatac gtgcggtcat ggtacgcatg tggct　　　　　　　45

<210> SEQ ID NO 84
<211> LENGTH: 45
<212> TYPE: DNA
<213> ORGANISM: Artificial
<220> FEATURE:
<223> OTHER INFORMATION: Oligonucleotide as PCR primer N66D_F

<400> SEQUENCE: 84
acgaataatg ccaatgatac ggatggtcat ggtacgcatg tggct　　　　　　　45

<210> SEQ ID NO 85
<211> LENGTH: 45
<212> TYPE: DNA
<213> ORGANISM: Artificial
<220> FEATURE:
<223> OTHER INFORMATION: Oligonucleotide as PCR primer N66E_F

<400> SEQUENCE: 85
acgaataatg ccaatgatac ggaaggtcat ggtacgcatg tggct　　　　　　　45

<210> SEQ ID NO 86
<211> LENGTH: 45
<212> TYPE: DNA
<213> ORGANISM: Artificial
<220> FEATURE:
<223> OTHER INFORMATION: Oligonucleotide as PCR primer N66F_F

<400> SEQUENCE: 86
acgaataatg ccaatgatac gttcggtcat ggtacgcatg tggct　　　　　　　45

<210> SEQ ID NO 87
<211> LENGTH: 45
<212> TYPE: DNA
<213> ORGANISM: Artificial
<220> FEATURE:
<223> OTHER INFORMATION: Oligonucleotide as PCR primer N66G_F

<400> SEQUENCE: 87
acgaataatg ccaatgatac gggaggtcat ggtacgcatg tggct　　　　　　　45

<210> SEQ ID NO 88
<211> LENGTH: 45

-continued

<212> TYPE: DNA
<213> ORGANISM: Artificial
<220> FEATURE:
<223> OTHER INFORMATION: Oligonucleotide as PCR primer N66H_F

<400> SEQUENCE: 88
acgaataatg ccaatgatac gcatggtcat ggtacgcatg tggct          45

<210> SEQ ID NO 89
<211> LENGTH: 45
<212> TYPE: DNA
<213> ORGANISM: Artificial
<220> FEATURE:
<223> OTHER INFORMATION: Oligonucleotide as PCR primer N66I_F

<400> SEQUENCE: 89
acgaataatg ccaatgatac gattggtcat ggtacgcatg tggct          45

<210> SEQ ID NO 90
<211> LENGTH: 45
<212> TYPE: DNA
<213> ORGANISM: Artificial
<220> FEATURE:
<223> OTHER INFORMATION: Oligonucleotide as PCR primer N66K_F

<400> SEQUENCE: 90
acgaataatg ccaatgatac gaaaggtcat ggtacgcatg tggct          45

<210> SEQ ID NO 91
<211> LENGTH: 45
<212> TYPE: DNA
<213> ORGANISM: Artificial
<220> FEATURE:
<223> OTHER INFORMATION: Oligonucleotide as PCR primer N66L_F

<400> SEQUENCE: 91
acgaataatg ccaatgatac gcttggtcat ggtacgcatg tggct          45

<210> SEQ ID NO 92
<211> LENGTH: 45
<212> TYPE: DNA
<213> ORGANISM: Artificial
<220> FEATURE:
<223> OTHER INFORMATION: Oligonucleotide as PCR primer N66M_F

<400> SEQUENCE: 92
acgaataatg ccaatgatac gatgggtcat ggtacgcatg tggct          45

<210> SEQ ID NO 93
<211> LENGTH: 45
<212> TYPE: DNA
<213> ORGANISM: Artificial
<220> FEATURE:
<223> OTHER INFORMATION: Oligonucleotide as PCR primer N66P_F

<400> SEQUENCE: 93
acgaataatg ccaatgatac gccaggtcat ggtacgcatg tggct          45

<210> SEQ ID NO 94
<211> LENGTH: 45
<212> TYPE: DNA
<213> ORGANISM: Artificial
<220> FEATURE:
<223> OTHER INFORMATION: Oligonucleotide as PCR primer N66Q_F

<400> SEQUENCE: 94

-continued acgaataatg ccaatgatac gcagggtcat ggtacgcatg tggct         45

<210> SEQ ID NO 95
<211> LENGTH: 45
<212> TYPE: DNA
<213> ORGANISM: Artificial
<220> FEATURE:
<223> OTHER INFORMATION: Oligonucleotide as PCR primer N66R_F

<400> SEQUENCE: 95
acgaataatg ccaatgatac gagaggtcat ggtacgcatg tggct         45

<210> SEQ ID NO 96
<211> LENGTH: 45
<212> TYPE: DNA
<213> ORGANISM: Artificial
<220> FEATURE:
<223> OTHER INFORMATION: Oligonucleotide as PCR primer N66S_F

<400> SEQUENCE: 96
acgaataatg ccaatgatac gtccggtcat ggtacgcatg tggct         45

<210> SEQ ID NO 97
<211> LENGTH: 45
<212> TYPE: DNA
<213> ORGANISM: Artificial
<220> FEATURE:
<223> OTHER INFORMATION: Oligonucleotide as PCR primer N66T_F

<400> SEQUENCE: 97
acgaataatg ccaatgatac gacaggtcat ggtacgcatg tggct         45

<210> SEQ ID NO 98
<211> LENGTH: 45
<212> TYPE: DNA
<213> ORGANISM: Artificial
<220> FEATURE:
<223> OTHER INFORMATION: Oligonucleotide as PCR primer N66V_F

<400> SEQUENCE: 98
acgaataatg ccaatgatac ggtgggtcat ggtacgcatg tggct         45

<210> SEQ ID NO 99
<211> LENGTH: 45
<212> TYPE: DNA
<213> ORGANISM: Artificial
<220> FEATURE:
<223> OTHER INFORMATION: Oligonucleotide as PCR primer N66W_F

<400> SEQUENCE: 99
acgaataatg ccaatgatac gtggggtcat ggtacgcatg tggct         45

<210> SEQ ID NO 100
<211> LENGTH: 45
<212> TYPE: DNA
<213> ORGANISM: Artificial
<220> FEATURE:
<223> OTHER INFORMATION: Oligonucleotide as PCR primer N66Y_F

<400> SEQUENCE: 100
acgaataatg ccaatgatac gtatggtcat ggtacgcatg tggct         45

<210> SEQ ID NO 101
<211> LENGTH: 21
<212> TYPE: DNA
<213> ORGANISM: Artificial

```
<220> FEATURE:
<223> OTHER INFORMATION: Oligonucleotide as PCR primer T82_R

<400> SEQUENCE: 101
ggagccgttt cctaatacgg a                                           21

<210> SEQ ID NO 102
<211> LENGTH: 45
<212> TYPE: DNA
<213> ORGANISM: Artificial
<220> FEATURE:
<223> OTHER INFORMATION: Oligonucleotide as PCR primer T82A_F

<400> SEQUENCE: 102
tccgtattag gaaacggctc cgcaaataaa ggaatggcgc ctcag                 45

<210> SEQ ID NO 103
<211> LENGTH: 45
<212> TYPE: DNA
<213> ORGANISM: Artificial
<220> FEATURE:
<223> OTHER INFORMATION: Oligonucleotide as PCR primer T82C_F

<400> SEQUENCE: 103
tccgtattag gaaacggctc ctgcaataaa ggaatggcgc ctcag                 45

<210> SEQ ID NO 104
<211> LENGTH: 45
<212> TYPE: DNA
<213> ORGANISM: Artificial
<220> FEATURE:
<223> OTHER INFORMATION: Oligonucleotide as PCR primer T82D_F

<400> SEQUENCE: 104
tccgtattag gaaacggctc cgataataaa ggaatggcgc ctcag                 45

<210> SEQ ID NO 105
<211> LENGTH: 45
<212> TYPE: DNA
<213> ORGANISM: Artificial
<220> FEATURE:
<223> OTHER INFORMATION: Oligonucleotide as PCR primer T82E_F

<400> SEQUENCE: 105
tccgtattag gaaacggctc cgaaaataaa ggaatggcgc ctcag                 45

<210> SEQ ID NO 106
<211> LENGTH: 45
<212> TYPE: DNA
<213> ORGANISM: Artificial
<220> FEATURE:
<223> OTHER INFORMATION: Oligonucleotide as PCR primer T82F_F

<400> SEQUENCE: 106
tccgtattag gaaacggctc cttcaataaa ggaatggcgc ctcag                 45

<210> SEQ ID NO 107
<211> LENGTH: 45
<212> TYPE: DNA
<213> ORGANISM: Artificial
<220> FEATURE:
<223> OTHER INFORMATION: Oligonucleotide as PCR primer T82G_F

<400> SEQUENCE: 107
tccgtattag gaaacggctc cggaaataaa ggaatggcgc ctcag                 45
```

<210> SEQ ID NO 108
<211> LENGTH: 45
<212> TYPE: DNA
<213> ORGANISM: Artificial
<220> FEATURE:
<223> OTHER INFORMATION: Oligonucleotide as PCR primer T82H_F

<400> SEQUENCE: 108
tccgtattag gaaacggctc ccataataaa ggaatggcgc ctcag        45

<210> SEQ ID NO 109
<211> LENGTH: 45
<212> TYPE: DNA
<213> ORGANISM: Artificial
<220> FEATURE:
<223> OTHER INFORMATION: Oligonucleotide as PCR primer T82I_F

<400> SEQUENCE: 109
tccgtattag gaaacggctc cattaataaa ggaatggcgc ctcag        45

<210> SEQ ID NO 110
<211> LENGTH: 45
<212> TYPE: DNA
<213> ORGANISM: Artificial
<220> FEATURE:
<223> OTHER INFORMATION: Oligonucleotide as PCR primer T82K_F

<400> SEQUENCE: 110
tccgtattag gaaacggctc caaaaataaa ggaatggcgc ctcag        45

<210> SEQ ID NO 111
<211> LENGTH: 45
<212> TYPE: DNA
<213> ORGANISM: Artificial
<220> FEATURE:
<223> OTHER INFORMATION: Oligonucleotide as PCR primer T82L_F

<400> SEQUENCE: 111
tccgtattag gaaacggctc ccttaataaa ggaatggcgc ctcag        45

<210> SEQ ID NO 112
<211> LENGTH: 45
<212> TYPE: DNA
<213> ORGANISM: Artificial
<220> FEATURE:
<223> OTHER INFORMATION: Oligonucleotide as PCR primer T82M_F

<400> SEQUENCE: 112
tccgtattag gaaacggctc catgaataaa ggaatggcgc ctcag        45

<210> SEQ ID NO 113
<211> LENGTH: 45
<212> TYPE: DNA
<213> ORGANISM: Artificial
<220> FEATURE:
<223> OTHER INFORMATION: Oligonucleotide as PCR primer T82N_F

<400> SEQUENCE: 113
tccgtattag gaaacggctc caataataaa ggaatggcgc ctcag        45

<210> SEQ ID NO 114
<211> LENGTH: 45
<212> TYPE: DNA
<213> ORGANISM: Artificial
<220> FEATURE:
<223> OTHER INFORMATION: Oligonucleotide as PCR primer T82P_F

<400> SEQUENCE: 114
tccgtattag gaaacggctc cccaaataaa ggaatggcgc ctcag          45

<210> SEQ ID NO 115
<211> LENGTH: 45
<212> TYPE: DNA
<213> ORGANISM: Artificial
<220> FEATURE:
<223> OTHER INFORMATION: Oligonucleotide as PCR primer T82Q_F

<400> SEQUENCE: 115
tccgtattag gaaacggctc ccagaataaa ggaatggcgc ctcag          45

<210> SEQ ID NO 116
<211> LENGTH: 45
<212> TYPE: DNA
<213> ORGANISM: Artificial
<220> FEATURE:
<223> OTHER INFORMATION: Oligonucleotide as PCR primer T82R_F

<400> SEQUENCE: 116
tccgtattag gaaacggctc cagaaataaa ggaatggcgc ctcag          45

<210> SEQ ID NO 117
<211> LENGTH: 45
<212> TYPE: DNA
<213> ORGANISM: Artificial
<220> FEATURE:
<223> OTHER INFORMATION: Oligonucleotide as PCR primer T82S_F

<400> SEQUENCE: 117
tccgtattag gaaacggctc ctccaataaa ggaatggcgc ctcag          45

<210> SEQ ID NO 118
<211> LENGTH: 45
<212> TYPE: DNA
<213> ORGANISM: Artificial
<220> FEATURE:
<223> OTHER INFORMATION: Oligonucleotide as PCR primer T82V_F

<400> SEQUENCE: 118
tccgtattag gaaacggctc cgtgaataaa ggaatggcgc ctcag          45

<210> SEQ ID NO 119
<211> LENGTH: 45
<212> TYPE: DNA
<213> ORGANISM: Artificial
<220> FEATURE:
<223> OTHER INFORMATION: Oligonucleotide as PCR primer T82W_F

<400> SEQUENCE: 119
tccgtattag gaaacggctc ctggaataaa ggaatggcgc ctcag          45

<210> SEQ ID NO 120
<211> LENGTH: 45
<212> TYPE: DNA
<213> ORGANISM: Artificial
<220> FEATURE:
<223> OTHER INFORMATION: Oligonucleotide as PCR primer T82Y_F

<400> SEQUENCE: 120
tccgtattag gaaacggctc ctataataaa ggaatggcgc ctcag          45

<210> SEQ ID NO 121

```
<211> LENGTH: 21
<212> TYPE: DNA
<213> ORGANISM: Artificial
<220> FEATURE:
<223> OTHER INFORMATION: Oligonucleotide as PCR primer N83_R

<400> SEQUENCE: 121
agtggagccg tttcctaata c                                          21

<210> SEQ ID NO 122
<211> LENGTH: 45
<212> TYPE: DNA
<213> ORGANISM: Artificial
<220> FEATURE:
<223> OTHER INFORMATION: Oligonucleotide as PCR primer N83A_F

<400> SEQUENCE: 122
gtattaggaa acggctccac tgcaaaagga atggcgcctc aggcg                45

<210> SEQ ID NO 123
<211> LENGTH: 45
<212> TYPE: DNA
<213> ORGANISM: Artificial
<220> FEATURE:
<223> OTHER INFORMATION: Oligonucleotide as PCR primer N83C_F

<400> SEQUENCE: 123
gtattaggaa acggctccac ttgcaaagga atggcgcctc aggcg                45

<210> SEQ ID NO 124
<211> LENGTH: 45
<212> TYPE: DNA
<213> ORGANISM: Artificial
<220> FEATURE:
<223> OTHER INFORMATION: Oligonucleotide as PCR primer N83D_F

<400> SEQUENCE: 124
gtattaggaa acggctccac tgataaagga atggcgcctc aggcg                45

<210> SEQ ID NO 125
<211> LENGTH: 45
<212> TYPE: DNA
<213> ORGANISM: Artificial
<220> FEATURE:
<223> OTHER INFORMATION: Oligonucleotide as PCR primer N83E_F

<400> SEQUENCE: 125
gtattaggaa acggctccac tgaaaaagga atggcgcctc aggcg                45

<210> SEQ ID NO 126
<211> LENGTH: 45
<212> TYPE: DNA
<213> ORGANISM: Artificial
<220> FEATURE:
<223> OTHER INFORMATION: Oligonucleotide as PCR primer N83F_F

<400> SEQUENCE: 126
gtattaggaa acggctccac tttcaaagga atggcgcctc aggcg                45

<210> SEQ ID NO 127
<211> LENGTH: 45
<212> TYPE: DNA
<213> ORGANISM: Artificial
<220> FEATURE:
<223> OTHER INFORMATION: Oligonucleotide as PCR primer N83G_F

<400> SEQUENCE: 127
```
gtattaggaa acggctccac tggaaaagga atggcgcctc aggcg          45

<210> SEQ ID NO 128
<211> LENGTH: 45
<212> TYPE: DNA
<213> ORGANISM: Artificial
<220> FEATURE:
<223> OTHER INFORMATION: Oligonucleotide as PCR primer N83H_F

<400> SEQUENCE: 128
gtattaggaa acggctccac tcataaagga atggcgcctc aggcg          45

<210> SEQ ID NO 129
<211> LENGTH: 45
<212> TYPE: DNA
<213> ORGANISM: Artificial
<220> FEATURE:
<223> OTHER INFORMATION: Oligonucleotide as PCR primer N83I_F

<400> SEQUENCE: 129
gtattaggaa acggctccac tattaaagga atggcgcctc aggcg          45

<210> SEQ ID NO 130
<211> LENGTH: 45
<212> TYPE: DNA
<213> ORGANISM: Artificial
<220> FEATURE:
<223> OTHER INFORMATION: Oligonucleotide as PCR primer N83K_F

<400> SEQUENCE: 130
gtattaggaa acggctccac taaaaaagga atggcgcctc aggcg          45

<210> SEQ ID NO 131
<211> LENGTH: 45
<212> TYPE: DNA
<213> ORGANISM: Artificial
<220> FEATURE:
<223> OTHER INFORMATION: Oligonucleotide as PCR primer N83L_F

<400> SEQUENCE: 131
gtattaggaa acggctccac tcttaaagga atggcgcctc aggcg          45

<210> SEQ ID NO 132
<211> LENGTH: 45
<212> TYPE: DNA
<213> ORGANISM: Artificial
<220> FEATURE:
<223> OTHER INFORMATION: Oligonucleotide as PCR primer N83M_F

<400> SEQUENCE: 132
gtattaggaa acggctccac tatgaaagga atggcgcctc aggcg          45

<210> SEQ ID NO 133
<211> LENGTH: 45
<212> TYPE: DNA
<213> ORGANISM: Artificial
<220> FEATURE:
<223> OTHER INFORMATION: Oligonucleotide as PCR primer N83P_F

<400> SEQUENCE: 133
gtattaggaa acggctccac tccaaaagga atggcgcctc aggcg          45

<210> SEQ ID NO 134
<211> LENGTH: 45
<212> TYPE: DNA

<213> ORGANISM: Artificial
<220> FEATURE:
<223> OTHER INFORMATION: Oligonucleotide as PCR primer N83Q_F

<400> SEQUENCE: 134
gtattaggaa acggctccac tcagaaagga atggcgcctc aggcg            45

<210> SEQ ID NO 135
<211> LENGTH: 45
<212> TYPE: DNA
<213> ORGANISM: Artificial
<220> FEATURE:
<223> OTHER INFORMATION: Oligonucleotide as PCR primer N83R_F

<400> SEQUENCE: 135
gtattaggaa acggctccac tagaaaagga atggcgcctc aggcg            45

<210> SEQ ID NO 136
<211> LENGTH: 45
<212> TYPE: DNA
<213> ORGANISM: Artificial
<220> FEATURE:
<223> OTHER INFORMATION: Oligonucleotide as PCR primer N83S_F

<400> SEQUENCE: 136
gtattaggaa acggctccac ttccaaagga atggcgcctc aggcg            45

<210> SEQ ID NO 137
<211> LENGTH: 45
<212> TYPE: DNA
<213> ORGANISM: Artificial
<220> FEATURE:
<223> OTHER INFORMATION: Oligonucleotide as PCR primer N83T_F

<400> SEQUENCE: 137
gtattaggaa acggctccac tacaaaagga atggcgcctc aggcg            45

<210> SEQ ID NO 138
<211> LENGTH: 45
<212> TYPE: DNA
<213> ORGANISM: Artificial
<220> FEATURE:
<223> OTHER INFORMATION: Oligonucleotide as PCR primer N83V_F

<400> SEQUENCE: 138
gtattaggaa acggctccac tgtgaaagga atggcgcctc aggcg            45

<210> SEQ ID NO 139
<211> LENGTH: 45
<212> TYPE: DNA
<213> ORGANISM: Artificial
<220> FEATURE:
<223> OTHER INFORMATION: Oligonucleotide as PCR primer N83W_F

<400> SEQUENCE: 139
gtattaggaa acggctccac ttggaaagga atggcgcctc aggcg            45

<210> SEQ ID NO 140
<211> LENGTH: 45
<212> TYPE: DNA
<213> ORGANISM: Artificial
<220> FEATURE:
<223> OTHER INFORMATION: Oligonucleotide as PCR primer N83Y_F

<400> SEQUENCE: 140
gtattaggaa acggctccac ttataaagga atggcgcctc aggcg            45

<210> SEQ ID NO 141
<211> LENGTH: 21
<212> TYPE: DNA
<213> ORGANISM: Artificial
<220> FEATURE:
<223> OTHER INFORMATION: Oligonucleotide as PCR primer Q204_R

<400> SEQUENCE: 141
tgccacatgg ttgatattgt c					21

<210> SEQ ID NO 142
<211> LENGTH: 45
<212> TYPE: DNA
<213> ORGANISM: Artificial
<220> FEATURE:
<223> OTHER INFORMATION: Oligonucleotide as PCR primer Q204A_F

<400> SEQUENCE: 142
gacaatatca accatgtggc agcattctct tcacgtggac cgaca					45

<210> SEQ ID NO 143
<211> LENGTH: 45
<212> TYPE: DNA
<213> ORGANISM: Artificial
<220> FEATURE:
<223> OTHER INFORMATION: Oligonucleotide as PCR primer Q204C_F

<400> SEQUENCE: 143
gacaatatca accatgtggc atgcttctct tcacgtggac cgaca					45

<210> SEQ ID NO 144
<211> LENGTH: 45
<212> TYPE: DNA
<213> ORGANISM: Artificial
<220> FEATURE:
<223> OTHER INFORMATION: Oligonucleotide as PCR primer Q204D_F

<400> SEQUENCE: 144
gacaatatca accatgtggc agatttctct tcacgtggac cgaca					45

<210> SEQ ID NO 145
<211> LENGTH: 45
<212> TYPE: DNA
<213> ORGANISM: Artificial
<220> FEATURE:
<223> OTHER INFORMATION: Oligonucleotide as PCR primer Q204E_F

<400> SEQUENCE: 145
gacaatatca accatgtggc agaattctct tcacgtggac cgaca					45

<210> SEQ ID NO 146
<211> LENGTH: 45
<212> TYPE: DNA
<213> ORGANISM: Artificial
<220> FEATURE:
<223> OTHER INFORMATION: Oligonucleotide as PCR primer Q204F_F

<400> SEQUENCE: 146
gacaatatca accatgtggc attcttctct tcacgtggac cgaca					45

<210> SEQ ID NO 147
<211> LENGTH: 45
<212> TYPE: DNA
<213> ORGANISM: Artificial
<220> FEATURE:

<223> OTHER INFORMATION: Oligonucleotide as PCR primer Q204G_F

<400> SEQUENCE: 147
gacaatatca accatgtggc aggattctct tcacgtggac cgaca          45

<210> SEQ ID NO 148
<211> LENGTH: 45
<212> TYPE: DNA
<213> ORGANISM: Artificial
<220> FEATURE:
<223> OTHER INFORMATION: Oligonucleotide as PCR primer Q204H_F

<400> SEQUENCE: 148
gacaatatca accatgtggc acatttctct tcacgtggac cgaca          45

<210> SEQ ID NO 149
<211> LENGTH: 45
<212> TYPE: DNA
<213> ORGANISM: Artificial
<220> FEATURE:
<223> OTHER INFORMATION: Oligonucleotide as PCR primer Q204I_F

<400> SEQUENCE: 149
gacaatatca accatgtggc aattttctct tcacgtggac cgaca          45

<210> SEQ ID NO 150
<211> LENGTH: 45
<212> TYPE: DNA
<213> ORGANISM: Artificial
<220> FEATURE:
<223> OTHER INFORMATION: Oligonucleotide as PCR primer Q204K_F

<400> SEQUENCE: 150
gacaatatca accatgtggc aaaattctct tcacgtggac cgaca          45

<210> SEQ ID NO 151
<211> LENGTH: 45
<212> TYPE: DNA
<213> ORGANISM: Artificial
<220> FEATURE:
<223> OTHER INFORMATION: Oligonucleotide as PCR primer Q204L_F

<400> SEQUENCE: 151
gacaatatca accatgtggc acttttctct tcacgtggac cgaca          45

<210> SEQ ID NO 152
<211> LENGTH: 45
<212> TYPE: DNA
<213> ORGANISM: Artificial
<220> FEATURE:
<223> OTHER INFORMATION: Oligonucleotide as PCR primer Q204M_F

<400> SEQUENCE: 152
gacaatatca accatgtggc aatgttctct tcacgtggac cgaca          45

<210> SEQ ID NO 153
<211> LENGTH: 45
<212> TYPE: DNA
<213> ORGANISM: Artificial
<220> FEATURE:
<223> OTHER INFORMATION: Oligonucleotide as PCR primer Q204N_F

<400> SEQUENCE: 153
gacaatatca accatgtggc aaattctct tcacgtggac cgaca          45

```
<210> SEQ ID NO 154
<211> LENGTH: 45
<212> TYPE: DNA
<213> ORGANISM: Artificial
<220> FEATURE:
<223> OTHER INFORMATION: Oligonucleotide as PCR primer Q204P_F

<400> SEQUENCE: 154
gacaatatca accatgtggc accattctct tcacgtggac cgaca          45

<210> SEQ ID NO 155
<211> LENGTH: 45
<212> TYPE: DNA
<213> ORGANISM: Artificial
<220> FEATURE:
<223> OTHER INFORMATION: Oligonucleotide as PCR primer Q204R_F

<400> SEQUENCE: 155
gacaatatca accatgtggc aagattctct tcacgtggac cgaca          45

<210> SEQ ID NO 156
<211> LENGTH: 45
<212> TYPE: DNA
<213> ORGANISM: Artificial
<220> FEATURE:
<223> OTHER INFORMATION: Oligonucleotide as PCR primer Q204S_F

<400> SEQUENCE: 156
gacaatatca accatgtggc atccttctct tcacgtggac cgaca          45

<210> SEQ ID NO 157
<211> LENGTH: 45
<212> TYPE: DNA
<213> ORGANISM: Artificial
<220> FEATURE:
<223> OTHER INFORMATION: Oligonucleotide as PCR primer Q204T_F

<400> SEQUENCE: 157
gacaatatca accatgtggc aacattctct tcacgtggac cgaca          45

<210> SEQ ID NO 158
<211> LENGTH: 45
<212> TYPE: DNA
<213> ORGANISM: Artificial
<220> FEATURE:
<223> OTHER INFORMATION: Oligonucleotide as PCR primer Q204V_F

<400> SEQUENCE: 158
gacaatatca accatgtggc agtgttctct tcacgtggac cgaca          45

<210> SEQ ID NO 159
<211> LENGTH: 45
<212> TYPE: DNA
<213> ORGANISM: Artificial
<220> FEATURE:
<223> OTHER INFORMATION: Oligonucleotide as PCR primer Q204W_F

<400> SEQUENCE: 159
gacaatatca accatgtggc atggttctct tcacgtggac cgaca          45

<210> SEQ ID NO 160
<211> LENGTH: 45
<212> TYPE: DNA
<213> ORGANISM: Artificial
<220> FEATURE:
<223> OTHER INFORMATION: Oligonucleotide as PCR primer Q204Y_F
```

<400> SEQUENCE: 160
gacaatatca accatgtggc atatttctct tcacgtggac cgaca       45

<210> SEQ ID NO 161
<211> LENGTH: 21
<212> TYPE: DNA
<213> ORGANISM: Artificial
<220> FEATURE:
<223> OTHER INFORMATION: Oligonucleotide as PCR primer A319_R

<400> SEQUENCE: 161
aacgttcagg gatttatcca a       21

<210> SEQ ID NO 162
<211> LENGTH: 45
<212> TYPE: DNA
<213> ORGANISM: Artificial
<220> FEATURE:
<223> OTHER INFORMATION: Oligonucleotide as PCR primer A319C_F

<400> SEQUENCE: 162
ttggataaat ccctgaacgt tgctatgtg aacgagtcca gttct       45

<210> SEQ ID NO 163
<211> LENGTH: 45
<212> TYPE: DNA
<213> ORGANISM: Artificial
<220> FEATURE:
<223> OTHER INFORMATION: Oligonucleotide as PCR primer A319D_F

<400> SEQUENCE: 163
ttggataaat ccctgaacgt tgattatgtg aacgagtcca gttct       45

<210> SEQ ID NO 164
<211> LENGTH: 45
<212> TYPE: DNA
<213> ORGANISM: Artificial
<220> FEATURE:
<223> OTHER INFORMATION: Oligonucleotide as PCR primer A319E_F

<400> SEQUENCE: 164
ttggataaat ccctgaacgt tgaatatgtg aacgagtcca gttct       45

<210> SEQ ID NO 165
<211> LENGTH: 45
<212> TYPE: DNA
<213> ORGANISM: Artificial
<220> FEATURE:
<223> OTHER INFORMATION: Oligonucleotide as PCR primer A319F_F

<400> SEQUENCE: 165
ttggataaat ccctgaacgt tttctatgtg aacgagtcca gttct       45

<210> SEQ ID NO 166
<211> LENGTH: 45
<212> TYPE: DNA
<213> ORGANISM: Artificial
<220> FEATURE:
<223> OTHER INFORMATION: Oligonucleotide as PCR primer A319G_F

<400> SEQUENCE: 166
ttggataaat ccctgaacgt tggatatgtg aacgagtcca gttct       45

<210> SEQ ID NO 167
<211> LENGTH: 45

```
<212> TYPE: DNA
<213> ORGANISM: Artificial
<220> FEATURE:
<223> OTHER INFORMATION: Oligonucleotide as PCR primer A319H_F

<400> SEQUENCE: 167
ttggataaat ccctgaacgt tcattatgtg aacgagtcca gttct          45

<210> SEQ ID NO 168
<211> LENGTH: 45
<212> TYPE: DNA
<213> ORGANISM: Artificial
<220> FEATURE:
<223> OTHER INFORMATION: Oligonucleotide as PCR primer A319I_F

<400> SEQUENCE: 168
ttggataaat ccctgaacgt tatttatgtg aacgagtcca gttct          45

<210> SEQ ID NO 169
<211> LENGTH: 45
<212> TYPE: DNA
<213> ORGANISM: Artificial
<220> FEATURE:
<223> OTHER INFORMATION: Oligonucleotide as PCR primer A319K_F

<400> SEQUENCE: 169
ttggataaat ccctgaacgt taaatatgtg aacgagtcca gttct          45

<210> SEQ ID NO 170
<211> LENGTH: 45
<212> TYPE: DNA
<213> ORGANISM: Artificial
<220> FEATURE:
<223> OTHER INFORMATION: Oligonucleotide as PCR primer A319L_F

<400> SEQUENCE: 170
ttggataaat ccctgaacgt tctttatgtg aacgagtcca gttct          45

<210> SEQ ID NO 171
<211> LENGTH: 45
<212> TYPE: DNA
<213> ORGANISM: Artificial
<220> FEATURE:
<223> OTHER INFORMATION: Oligonucleotide as PCR primer A319M_F

<400> SEQUENCE: 171
ttggataaat ccctgaacgt tatgtatgtg aacgagtcca gttct          45

<210> SEQ ID NO 172
<211> LENGTH: 45
<212> TYPE: DNA
<213> ORGANISM: Artificial
<220> FEATURE:
<223> OTHER INFORMATION: Oligonucleotide as PCR primer A319N_F

<400> SEQUENCE: 172
ttggataaat ccctgaacgt taattatgtg aacgagtcca gttct          45

<210> SEQ ID NO 173
<211> LENGTH: 45
<212> TYPE: DNA
<213> ORGANISM: Artificial
<220> FEATURE:
<223> OTHER INFORMATION: Oligonucleotide as PCR primer A319P_F

<400> SEQUENCE: 173
```
ttggataaat ccctgaacgt tccatatgtg aacgagtcca gttct   45

<210> SEQ ID NO 174
<211> LENGTH: 45
<212> TYPE: DNA
<213> ORGANISM: Artificial
<220> FEATURE:
<223> OTHER INFORMATION: Oligonucleotide as PCR primer A319Q_F

<400> SEQUENCE: 174
ttggataaat ccctgaacgt tcagtatgtg aacgagtcca gttct   45

<210> SEQ ID NO 175
<211> LENGTH: 45
<212> TYPE: DNA
<213> ORGANISM: Artificial
<220> FEATURE:
<223> OTHER INFORMATION: Oligonucleotide as PCR primer A319R_F

<400> SEQUENCE: 175
ttggataaat ccctgaacgt tagatatgtg aacgagtcca gttct   45

<210> SEQ ID NO 176
<211> LENGTH: 45
<212> TYPE: DNA
<213> ORGANISM: Artificial
<220> FEATURE:
<223> OTHER INFORMATION: Oligonucleotide as PCR primer A319S_F

<400> SEQUENCE: 176
ttggataaat ccctgaacgt ttcctatgtg aacgagtcca gttct   45

<210> SEQ ID NO 177
<211> LENGTH: 45
<212> TYPE: DNA
<213> ORGANISM: Artificial
<220> FEATURE:
<223> OTHER INFORMATION: Oligonucleotide as PCR primer A319T_F

<400> SEQUENCE: 177
ttggataaat ccctgaacgt tacatatgtg aacgagtcca gttct   45

<210> SEQ ID NO 178
<211> LENGTH: 45
<212> TYPE: DNA
<213> ORGANISM: Artificial
<220> FEATURE:
<223> OTHER INFORMATION: Oligonucleotide as PCR primer A319V_F

<400> SEQUENCE: 178
ttggataaat ccctgaacgt tgtgtatgtg aacgagtcca gttct   45

<210> SEQ ID NO 179
<211> LENGTH: 45
<212> TYPE: DNA
<213> ORGANISM: Artificial
<220> FEATURE:
<223> OTHER INFORMATION: Oligonucleotide as PCR primer A319W_F

<400> SEQUENCE: 179
ttggataaat ccctgaacgt ttggtatgtg aacgagtcca gttct   45

<210> SEQ ID NO 180
<211> LENGTH: 45
<212> TYPE: DNA
<213> ORGANISM: Artificial

```
<220> FEATURE:
<223> OTHER INFORMATION: Oligonucleotide as PCR primer A319Y_F

<400> SEQUENCE: 180
ttggataaat ccctgaacgt ttattatgtg aacgagtcca gttct            45

<210> SEQ ID NO 181
<211> LENGTH: 21
<212> TYPE: DNA
<213> ORGANISM: Artificial
<220> FEATURE:
<223> OTHER INFORMATION: Oligonucleotide as PCR primer F337_R

<400> SEQUENCE: 181
cgagtacgtc gcttttggc t                                       21

<210> SEQ ID NO 182
<211> LENGTH: 45
<212> TYPE: DNA
<213> ORGANISM: Artificial
<220> FEATURE:
<223> OTHER INFORMATION: Oligonucleotide as PCR primer F337A_F

<400> SEQUENCE: 182
agccaaaaag cgacgtactc ggcaactgct actgccggca agcct            45

<210> SEQ ID NO 183
<211> LENGTH: 45
<212> TYPE: DNA
<213> ORGANISM: Artificial
<220> FEATURE:
<223> OTHER INFORMATION: Oligonucleotide as PCR primer F337C_F

<400> SEQUENCE: 183
agccaaaaag cgacgtactc gtgcactgct actgccggca agcct            45

<210> SEQ ID NO 184
<211> LENGTH: 45
<212> TYPE: DNA
<213> ORGANISM: Artificial
<220> FEATURE:
<223> OTHER INFORMATION: Oligonucleotide as PCR primer F337D_F

<400> SEQUENCE: 184
agccaaaaag cgacgtactc ggatactgct actgccggca agcct            45

<210> SEQ ID NO 185
<211> LENGTH: 45
<212> TYPE: DNA
<213> ORGANISM: Artificial
<220> FEATURE:
<223> OTHER INFORMATION: Oligonucleotide as PCR primer F337E_F

<400> SEQUENCE: 185
agccaaaaag cgacgtactc ggaaactgct actgccggca agcct            45

<210> SEQ ID NO 186
<211> LENGTH: 45
<212> TYPE: DNA
<213> ORGANISM: Artificial
<220> FEATURE:
<223> OTHER INFORMATION: Oligonucleotide as PCR primer F337G_F

<400> SEQUENCE: 186
agccaaaaag cgacgtactc gggaactgct actgccggca agcct            45
```

<210> SEQ ID NO 187
<211> LENGTH: 45
<212> TYPE: DNA
<213> ORGANISM: Artificial
<220> FEATURE:
<223> OTHER INFORMATION: Oligonucleotide as PCR primer F337H_F

<400> SEQUENCE: 187
agccaaaaag cgacgtactc gcatactgct actgccggca agcct           45

<210> SEQ ID NO 188
<211> LENGTH: 45
<212> TYPE: DNA
<213> ORGANISM: Artificial
<220> FEATURE:
<223> OTHER INFORMATION: Oligonucleotide as PCR primer F337I_F

<400> SEQUENCE: 188
agccaaaaag cgacgtactc gattactgct actgccggca agcct           45

<210> SEQ ID NO 189
<211> LENGTH: 45
<212> TYPE: DNA
<213> ORGANISM: Artificial
<220> FEATURE:
<223> OTHER INFORMATION: Oligonucleotide as PCR primer F337K_F

<400> SEQUENCE: 189
agccaaaaag cgacgtactc gaaaactgct actgccggca agcct           45

<210> SEQ ID NO 190
<211> LENGTH: 45
<212> TYPE: DNA
<213> ORGANISM: Artificial
<220> FEATURE:
<223> OTHER INFORMATION: Oligonucleotide as PCR primer F337L_F

<400> SEQUENCE: 190
agccaaaaag cgacgtactc gcttactgct actgccggca agcct           45

<210> SEQ ID NO 191
<211> LENGTH: 45
<212> TYPE: DNA
<213> ORGANISM: Artificial
<220> FEATURE:
<223> OTHER INFORMATION: Oligonucleotide as PCR primer F337M_F

<400> SEQUENCE: 191
agccaaaaag cgacgtactc gatgactgct actgccggca agcct           45

<210> SEQ ID NO 192
<211> LENGTH: 45
<212> TYPE: DNA
<213> ORGANISM: Artificial
<220> FEATURE:
<223> OTHER INFORMATION: Oligonucleotide as PCR primer F337N_F

<400> SEQUENCE: 192
agccaaaaag cgacgtactc gaatactgct actgccggca agcct           45

<210> SEQ ID NO 193
<211> LENGTH: 45
<212> TYPE: DNA
<213> ORGANISM: Artificial
<220> FEATURE:
<223> OTHER INFORMATION: Oligonucleotide as PCR primer F337P_F

```
<400> SEQUENCE: 193
agccaaaaag cgacgtactc gccaactgct actgccggca agcct            45

<210> SEQ ID NO 194
<211> LENGTH: 45
<212> TYPE: DNA
<213> ORGANISM: Artificial
<220> FEATURE:
<223> OTHER INFORMATION: Oligonucleotide as PCR primer F337Q_F

<400> SEQUENCE: 194
agccaaaaag cgacgtactc gcagactgct actgccggca agcct            45

<210> SEQ ID NO 195
<211> LENGTH: 45
<212> TYPE: DNA
<213> ORGANISM: Artificial
<220> FEATURE:
<223> OTHER INFORMATION: Oligonucleotide as PCR primer F337R_F

<400> SEQUENCE: 195
agccaaaaag cgacgtactc gagaactgct actgccggca agcct            45

<210> SEQ ID NO 196
<211> LENGTH: 45
<212> TYPE: DNA
<213> ORGANISM: Artificial
<220> FEATURE:
<223> OTHER INFORMATION: Oligonucleotide as PCR primer F337S_F

<400> SEQUENCE: 196
agccaaaaag cgacgtactc gtccactgct actgccggca agcct            45

<210> SEQ ID NO 197
<211> LENGTH: 45
<212> TYPE: DNA
<213> ORGANISM: Artificial
<220> FEATURE:
<223> OTHER INFORMATION: Oligonucleotide as PCR primer F337T_F

<400> SEQUENCE: 197
agccaaaaag cgacgtactc gacaactgct actgccggca agcct            45

<210> SEQ ID NO 198
<211> LENGTH: 45
<212> TYPE: DNA
<213> ORGANISM: Artificial
<220> FEATURE:
<223> OTHER INFORMATION: Oligonucleotide as PCR primer F337V_F

<400> SEQUENCE: 198
agccaaaaag cgacgtactc ggtgactgct actgccggca agcct            45

<210> SEQ ID NO 199
<211> LENGTH: 45
<212> TYPE: DNA
<213> ORGANISM: Artificial
<220> FEATURE:
<223> OTHER INFORMATION: Oligonucleotide as PCR primer F337W_F

<400> SEQUENCE: 199
agccaaaaag cgacgtactc gtggactgct actgccggca agcct            45

<210> SEQ ID NO 200
```

```
<211> LENGTH: 45
<212> TYPE: DNA
<213> ORGANISM: Artificial
<220> FEATURE:
<223> OTHER INFORMATION: Oligonucleotide as PCR primer F337Y_F

<400> SEQUENCE: 200
agccaaaaag cgacgtactc gtatactgct actgccggca agcct          45
```

ALKALINE PROTEASE VARIANTS

REFERENCE TO SEQUENCE LISTING SUBMITTED ELECTRONICALLY

The content of the electronically submitted substitute sequence listing, file name sequencelisting.txt; size 46,859 bytes; and date of creation Oct. 26, 2011, filed herewith, is incorporated herein by reference in its entirety.

FIELD OF THE INVENTION

The present invention relates to alkaline protease variants which are useful enzymes incorporated into liquid detergents, and to genes encoding the same.

BACKGROUND OF THE INVENTION

Proteases have long been employed in industry for a wide variety of products, including detergents (e.g., laundry detergents), fiber-modifying agents, leather treatment agents, cosmetics, bath agents, food-modifying agents, and drugs. Among these, proteases for detergents are industrially produced in the greatest amounts. Examples of such proteases known heretofore include Alcalase®, Savinase® (Novozymes), Maxacal® (Genencor), Blap® (Henkel), and KAP (Kao Corporation).

Protease is incorporated into a laundry detergent for providing the detergent with the ability to degrade dirt mainly composed of protein and deposited on clothing into low-molecular-weight products, to thereby promote solubilization of the thus-degraded products with a surfactant. However, in actuality, such deposited dirt is complex dirt containing, in addition to proteins, a plurality of organic and inorganic components such as sebum-derived lipid and solid particles. Therefore, there is a continuous demand for a detergent exhibiting excellent detergency to such complex dirt.

In view of the foregoing, the present inventors previously discovered several alkaline proteases having a molecular weight of about 43,000, which maintain sufficient casein-degrading activity even in the presence of a fatty acid of high concentration and which exhibit excellent detergency to complex dirt containing proteins and sebum; and previously filed a patent application on the alkaline proteases (Patent Document 1). These alkaline proteases differ from conventionally known subtilisin, a serine protease derived from bacteria belonging to the genus *Bacillus*, in terms of molecular weight, primary structure, and enzymological characteristics, and having a very strong resistance to oxidizer. These alkaline proteases are suggested to be classified into a new subtilisin subfamily (Non-Patent Document 1).

Meanwhile, detergents can be categorized, by form thereof, into powder detergents and liquid detergents. Advantageously, liquid detergents have solubility higher than that of powder detergents, and neat liquid thereof can be directly applied to dirt. Although liquid detergents have such merits while powder detergents do not possess, liquid detergents are widely known to encounter technical difficulty in stable incorporation of an enzyme such as protease, while powder detergents do not encounter. Generally, since liquid detergents are stored at ambient temperature, the enzyme (protein) is readily denatured. In addition, liquid detergents contain a surfactant, fatty acid, solvent, etc., and the pH thereof falls within a weak alkaline range. Such conditions are very severe conditions for the enzyme. Furthermore, the protease, which is a proteolytic enzyme, undergoes problematic self-digestion, further reducing storage stability of the enzyme in liquid detergents.

In order to solve the aforementioned technical problems, there have been widely known addition of an enzyme-stabilizing agent such as calcium ion, borax, boric acid, a boron compound, a carboxylic acid (e.g., formic acid), or a polyol. Some studies have been carried out to cope with the problem of self-digestion based on inhibition of protease activity. Specifically, there have been reported methods for stabilizing protease through reversible inhibition of protease activity by use of 4-substituted phenylboronic acid (Patent Document 2) or a certain peptide-aldehyde and a boron composition (Patent Document 3). Also reported is that dextran-modified protease enhances stability of protease in aqueous solution containing a surfactant (Non-Patent Document 2).

However, the protease-stabilizing effect due to addition of an enzyme-stabilizing agent (e.g., calcium ion or boric acid) is insufficient, and the inhibitory effect varies depending on the type of protease. Furthermore, use of such agents increases production cost. Thus, these countermeasures are not thought to be best solutions for the problems involved in liquid detergents. Chemical modification of the enzyme also has problems in terms of production cost.

Generally, a surfactant, an alkaline agent, an anti-redeposition agent, solvent, perfume, a fluorescent dye, etc, are added to liquid detergents. Among these additives, a surfactant most severely impairs the stability of enzymes. Typically, an anionic surfactant and a nonionic surfactant are used in combination. Although a nonionic surfactant does not greatly damage enzymes, an anionic surfactant is thought to greatly damage enzymes, since the anionic surfactant enters the enzyme via its hydrophobic moiety and breaks hydrophobic interaction of the enzyme as well as traps divalent metal ions (e.g., calcium ions) which stabilize the enzyme (Non-Patent Document 3). Thus, enhancement of resistance of the enzyme to anionic surfactants is a very important factor for enhancing the stability of the enzyme in liquid detergents.

In an alkaline protease derived from KP43 [*Bacillus* sp. KSM-KP43 (FERN BP-6532)], the specific activity to the activity of the parent alkaline protease is known to be enhanced through substitution of the amino acid residue at the position 15 of the amino acid sequence with a histidine residue; substitution of the amino acid residue at the position 16 of the amino acid sequence with a threonine or glutamine residue (Patent Document 4); substitution of the amino acid residue at the position 65 of the amino acid sequence with a proline residue (Patent Document 5); or substitution of the amino acid residue at the position 66 of the amino acid sequence with an aspartic acid residue (Patent Document 6). However, there has never been known an alkaline protease variant which enhances the stability of an alkaline protease derived from KP43 in liquid detergents without reducing the specific activity.

Patent Document 1: WO 99/18218 pamphlet
Patent Document 2: JP-A-H11-507680
Patent Document 3: JP-A-2000-506933
Patent Document 4: JP-A-2004-305176
Patent Document 5: JP-A-2004-000122
Patent Document 6: JP-A-2002-218989
Non-Patent Document 1: Saeki et al., Biochem. Biophys. Res. Commun., 279, 313-319, 2000
Non-Patent Document 2: Cosmetics & Toiletries magazine, 111, p. 79-88, 1996
Non-Patent Document 3: Detergent Enzyme: A Challenge! In Handbook of Detergents part A, New York, p. 639-690, 1999

SUMMARY OF THE INVENTION

The present invention is directed to an alkaline protease variant derived from an alkaline protease consisting of an amino acid sequence represented by SEQ ID NO: 2 or consisting of an amino acid sequence having an identity of 90% or more therewith, wherein one or more amino acid residues at positions selected from (a) position 6, (b) position 15, (c) position 16, (d) position 65, (e) position 66, (f) position 82, (g) position 83, (h) position 204, (i) position 319, and (j) position 337 of the amino acid sequence represented by SEQ ID NO: 2, or at positions corresponding thereto are substituted with the following amino acid residues:

(a) or a position corresponding thereto: tryptophan, leucine, valine, isoleucine, methionine, tyrosine, glutamine, lysine, threonine, phenylalanine, arginine, serine, cysteine, alanine, or histidine;

(b) or a position corresponding thereto: glutamic acid, methionine, aspartic acid, valine, glutamine, arginine, cysteine, tryptophan, alanine, or phenylalanine;

(c) or a position corresponding thereto: methionine, glutamic acid, arginine, valine, lysine, phenylalanine, tyrosine, isoleucine, histidine, aspartic acid, or cysteine;

(d) or a position corresponding thereto: tryptophan;

(e) or a position corresponding thereto: histidine, tryptophan, serine, or leucine;

(f) or a position corresponding thereto: alanine, glutamic acid, glutamine, serine, cysteine, glycine, histidine, lysine, arginine, methionine, or asparagine;

(g) or a position corresponding thereto: alanine, serine, or cysteine;

(h) or a position corresponding thereto: glutamic acid, aspartic acid, cysteine, valine, threonine, proline, histidine, isoleucine, tryptophan, serine, asparagine, lysine or, arginine;

(i) or a position corresponding thereto: tryptophan, valine, threonine, leucine, isoleucine, cysteine, glutamic acid, lysine, tyrosine, arginine, phenylalanine, glutamine, methionine, proline, aspartic acid, asparagine, histidine, or serine; and (j) or a position corresponding thereto: arginine, glycine, serine, lysine, glutamine, threonine, histidine, alanine, cysteine, or valine.

The present invention is also directed to a gene encoding the alkaline protease variant.

The present invention is also directed to a recombinant vector including the gene.

The present invention is also directed to a transformant including the recombinant vector.

The present invention is also directed to a detergent composition including the alkaline protease variant.

The present invention is also directed to a method for enhancing the stability of an alkaline protease in a liquid detergent, the method including, in an alkaline protease consisting of an amino acid sequence represented by SEQ ID NO: 2 or consisting of an amino acid sequence having an identity of 90% or more therewith, substituting one or more amino acid residues at positions selected from (a) position 6, (b) position 15, (c) position 16, (d) position 65, (e) position 66, (f) position 82, (g) position 83, (h) position 204, (i) position 319, and (j) position 337 of the amino acid sequence represented by SEQ ID NO: 2, or at positions corresponding thereto with the following amino acid residues:

(a) or a position corresponding thereto: tryptophan, leucine, valine, isoleucine, methionine, tyrosine, glutamine, lysine, threonine, phenylalanine, arginine, serine, cysteine, alanine, or histidine;

(b) or a position corresponding thereto: glutamic acid, methionine, aspartic acid, valine, glutamine, arginine, cysteine, tryptophan, alanine, or phenylalanine;

(c) or a position corresponding thereto: methionine, glutamic acid, arginine, valine, lysine, phenylalanine, tyrosine, isoleucine, histidine, aspartic acid, or cysteine;

(d) or a position corresponding thereto: tryptophan;

(e) or a position corresponding thereto: histidine, tryptophan, serine, or leucine;

(f) or a position corresponding thereto: alanine, glutamic acid, glutamine, serine, cysteine, glycine, histidine, lysine, arginine, methionine, or asparagine;

(g) or a position corresponding thereto: alanine, serine, or cysteine;

(h) or a position corresponding thereto: glutamic acid, aspartic acid, cysteine, valine, threonine, proline, histidine, isoleucine, tryptophan, serine, asparagine, lysine or, arginine;

(i) or a position corresponding thereto: tryptophan, valine, threonine, leucine, isoleucine, cysteine, glutamic acid, lysine, tyrosine, arginine, phenylalanine, glutamine, methionine, proline, aspartic acid, asparagine, histidine, or serine; and (j) or a position corresponding thereto: arginine, glycine, serine, lysine, glutamine, threonine, histidine, alanine, cysteine, or valine.

DETAILED DESCRIPTION OF THE INVENTION

Figure 1:
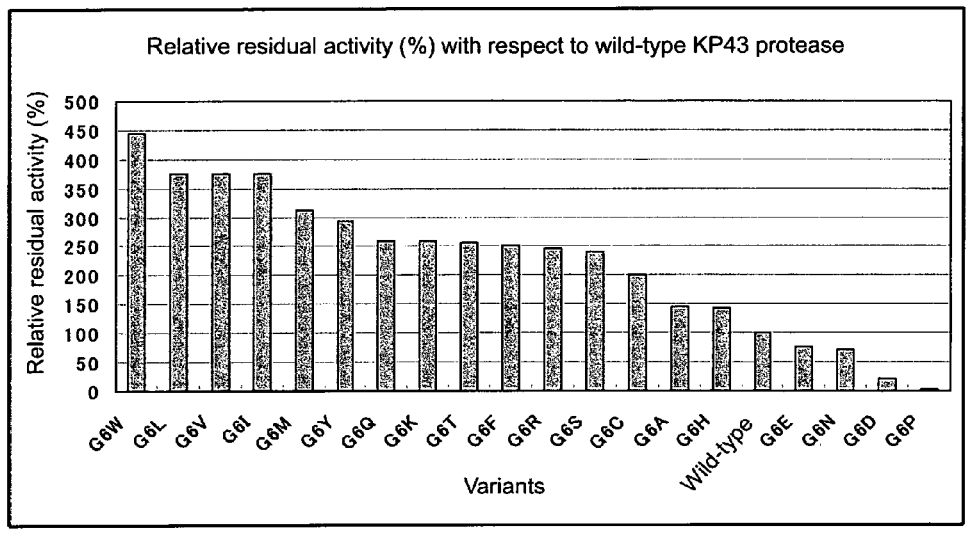
FIG. 1 A graph showing relative residual activities of variants in which the amino acid residue at the position 6 has been substituted.

The present invention is directed to provision of an alkaline protease variant having an enhanced stability in liquid detergents.

The present inventors have found that, through substituting specific amino acid residue(s) among the amino Acid residues characteristic to alkaline protease KP43 having a molecular weight of about 43,000 by other amino acid residues, the stability of the obtained alkaline protease variant in a liquid detergent is enhanced as compared with the parent alkaline protease.

The present invention can provide an alkaline protease variant which maintains activity in a liquid detergent containing an anionic surfactant such as LAS, which has high specific activity, and which serves as a useful enzyme for detergents.

The alkaline protease variant of the present invention is an alkaline protease variant derived from an alkaline protease consisting of an amino acid sequence represented by SEQ ID NO: 2 or consisting of an amino acid sequence having an identity of 90% or more therewith, wherein one or more amino acid residues at a position selected from (a) position 6, (b) position 15, (c) position 16, (d) position 65, (e) position 66, (f) position 82, (g) position 83, (h) position 204, (i) position 319, and (j) position 337 of the amino acid sequence represented by SEQ ID NO: 2, or at positions corresponding thereto are substituted with other amino acid residues. The alkaline protease variant of the present invention may be a wild-type variant or an artificially created variant.

In the present invention, examples of the alkaline protease consisting of the amino acid sequence represented by SEQ ID NO: 2 include an alkaline protease derived from KP43 [*Bacillus* sp. KSM-KP43 (FERM BP-6532)] (WO 99/18218 pamphlet).

Examples of the alkaline protease consisting of an amino acid sequence having an identity of 90% or more with the amino acid sequence represented by SEQ ID NO: 2 include those consisting of an amino acid sequence which differs from the amino acid sequence represented by SEQ ID NO: 2 but which has an identity of 90% or more, preferably 95% or more, more preferably 96% or more, even more preferably 97% or more, even more preferably 98% or more, even more preferably 99% or more with an amino acid sequence represented by SEQ ID NO: 2; or those consisting of a amino acid sequence represented by SEQ ID NO: 2, wherein one to several amino acids are deleted, substituted or added.

Preferably, these alkaline proteases have a function equivalent to or higher than that of the alkaline protease consisting of the amino acid sequence represented by SEQ ID NO: 2.

Specific examples of the alkaline protease consisting of an amino acid sequence having an identity of 90% or more with the amino acid sequence represented by SEQ ID NO: 2 include protease KP9860 [protease derived from *Bacillus* sp. KSM-KP9860 (FERM BP-6534), WO 99/18218, GenBank accession no. AB046403] and protease 9865 [protease derived from *Bacillus* sp. KSM-9865 (FERM BP-10139), GenBank accession no. AB084155].

Specific examples of the alkaline protease consisting of an amino acid sequence having an identity of 90% or more with the amino acid sequence represented by SEQ ID NO: 2 also include variants such as a variant consisting of an amino acid sequence represented by SEQ ID NO: 2 in which the amino acid residues at the positions 66 and 246 have been substituted with aspartic acid and serine, respectively, a variant consisting of an amino acid sequence represented by SEQ ID NO: 2 in which the amino acid residue at the position 103 has been substituted with arginine, and a variant consisting of an amino acid sequence represented by SEQ ID NO: 2 in which the acid residue at the position 195 has been substituted with alanine, glutamic acid, glutamine, valine, glycine, lysine, threonine, cysteine, proline, serine, arginine, asparagine, or histidine (JP-A-2002-218989); variants such as a variant consisting of an amino acid sequence represented by SEQ ID NO: 2 in which the amino acid residue at the position 84 has been substituted with arginine, a variant consisting of an amino acid sequence represented by SEQ ID NO: 2 in which the amino acid residue at the position 104 has been substituted with proline, a variant consisting of an amino acid sequence represented by SEQ ID NO: 2 in which the amino acid residue at the position 256 has been substituted with alanine or serine, and a variant consisting of an amino acid sequence represented by SEQ ID NO: 2 in which the amino acid residue at the position 369 has been substituted with asparagine (JP-A-2002-306176); variants such as a variant consisting of an amino acid sequence represented by SEQ ID NO: 2 in which the amino acid residue at the position 251 has been substituted with glutamine, valine, isoleucine, or threonine, and a variant consisting of an amino acid sequence represented by SEQ ID NO: 2 in which the amino acid residue at the position 256 has been substituted with glutamine, alanine, valine, serine, or asparagine (JP-A-2003-125783); variants such as a variant consisting of an amino acid sequence represented by SEQ ID NO: 2 in which the amino acid residue at the position 65 has been substituted with proline, a variant consisting of an amino acid sequence represented by SEQ ID NO: 2 in which the amino acid residue at the position 273 has been substituted with threonine or isoleucine, a variant consisting of an amino acid sequence represented by SEQ ID NO: 2 in which the amino acid residue at the position 320 has been substituted with phenylalanine or isoleucine, a variant consisting of an amino acid sequence represented by SEQ ID NO: 2 in which the amino acid residue at the position 356 has been substituted with glutamine or serine, and a variant consisting of an amino acid sequence represented by SEQ ID NO: 2 in which the amino acid residue at the position 387 has been substituted with lysine, alanine, or glutamine (JP-A-2004-000122); variants such as a variant consisting of an amino acid sequence represented by SEQ ID NO: 2 in which the amino acid residue at the position 163 has been substituted with histidine, isoleucine, leucine, threonine, valine, lysine, glutamine, aspartic acid, alanine, or phenylalanine, a variant consisting of an amino acid sequence represented by SEQ ID NO: 2 in which the amino acid residue at the position 170 has been substituted with valine or leucine, and a variant consisting of an amino acid sequence represented by SEQ ID NO: 2 in which the amino acid residue at the position 171 has been substituted with alanine, glycine, or threonine (JP-A-2004-057195); variants such as a variant consisting of an amino acid sequence represented by SEQ ID NO: 2 in which the amino acid residue at the position 63 has been substituted with serine, a variant consisting of an amino acid sequence represented by SEQ ID NO: 2 in which the amino acid residue at the position 89 has been substituted with histidine, a variant consisting of an amino acid sequence represented by SEQ ID NO: 2 in which the amino acid residue at the position 120 has been substituted with arginine, a variant consisting of an amino acid sequence represented by SEQ ID NO: 2 in which the amino acid residues at the positions 63 and 187 have been substituted with serine, a variant consisting of an amino acid sequence represented by SEQ ID NO: 2 in which the amino acid residue at the position 226 has been substituted with tyrosine, a variant consisting of an amino acid sequence represented by SEQ ID NO: 2 in which the amino acid residue at the position 296 has been substituted with valine, and a variant consisting of an amino acid sequence represented by SEQ ID NO: 2 in which the amino acid residue at the position 304 has been substituted with serine (JP-A-2004-305175); variants such as a variant consisting of an amino acid sequence represented by SEQ ID NO: 2 in which the amino acid residue at the position 15 has been substituted with histidine, a variant consisting of an amino acid sequence represented by SEQ ID NO: 2 in which the amino acid residue at the position 16 has been substituted with threonine or glutamine, a variant consisting of an amino acid sequence represented by SEQ ID NO: 2 in which the amino acid residue at the position 166 has been substituted with glycine, a variant consisting of an amino acid sequence represented by SEQ ID NO: 2 in which the amino acid residue at the position 167 has been substituted with valine, a variant consisting of an amino acid sequence represented by SEQ ID NO: 2 in which the amino acid residue at the position 346 has been substituted with arginine, and a variant consisting of an amino acid sequence represented by SEQ ID NO: 2 in which the amino acid residue at the position 405 has been substituted with aspartic acid (JP-A-2004-305176); and variants having a plurality of the aforementioned variations.

Among the aforementioned alkaline proteases and protease variants, preferred are those having any of the following enzymatic properties which the alkaline protease consisting of an amino acid sequence represented by SEQ ID NO:2 has:

1) having oxidizer resistance and acting and being stable in an alkaline pH region (≥8). As used herein, the expression "the alkaline protease exhibits oxidizer resistance" refers to the case where, after the alkaline protease is allowed to stand at 20° C. for 20 minutes in a 20 mM Britton-Robinson buffer (pH 10) containing hydrogen peroxide (50 mM) and calcium chloride (5 mM), the alkaline protease exhibits at least 50% residual activity (synthetic substrate method);

2) exhibiting at least 80% residual activity after treatment at 50° C. and a pH of 10 for 10 minutes;

3) inhibited by diisopropylfluorophosphoric acid (DFP) or phenylmethanesulfonyl fluoride (PMSF); and 4) having a molecular weight of 43,000±2,000 determined by SDS-PAGE.

In the present specification, the identity between amino acid sequences is calculated through the Lipman-Pearson method (Science, 227, 1435, (1985)). Specifically, the identity is calculated through analysis by use of a Search homology program of genetic information processing software Genetyx-Win (Ver. 5.1.1; Software Development Co., Ltd.), wherein the unit size to compare (ktup) is taken as 2.

In the present specification, the amino acid sequence in which one to several amino acids are deleted, substituted, or added is preferably an amino acid sequence in which one to ten amino acids are deleted, substituted, or added. The addition includes addition of one to several amino acids to both terminuses.

The alkaline protease variant of the present invention includes alkaline protease variants each consisting of an amino acid sequence represented by SEQ ID NO: 2 in which (a') the amino acid residue at the position 6 (glycine residue) has been substituted with tryptophan, leucine, valine, isoleucine, methionine, tyrosine, glutamine, lysine, threonine, phenylalanine, arginine, serine, cysteine, alanine, or histidine; (b') the amino acid residue at the position 15 (serine residue) has been substituted with glutamic acid, methionine, aspartic acid, valine, glutamine, arginine, cysteine, tryptophan, alanine, or phenylalanine; (c') the amino acid residue at the position 16 (serine residue) has been substituted with methionine, glutamic acid, arginine, valine, lysine, phenylalanine, tyrosine, isoleucine, histidine, aspartic acid, or cysteine; (d') the amino acid residue at the position 65 (threonine residue) has been substituted with tryptophan; (e') the amino acid residue at the position 66 (asparagine residue) has been substituted with histidine, tryptophan, serine, or leucine; (f') the amino acid residue at the position 82 (threonine residue) has been substituted with alanine, glutamic acid, glutamine, serine, cysteine, glycine, histidine, lysine, arginine, methionine, or asparagine; (g') the amino acid residue at the position 83 (asparagine residue) has been substituted with alanine, serine, or cysteine; (h') the amino acid residue at the position 204 (glutamine residue) has been substituted with glutamic acid, aspartic acid, cysteine, valine, threonine, proline, histidine, isoleucine, tryptophan, serine, asparagine, lysine, or arginine; (i') the amino acid residue at the position 319 (alanine residue) has been substituted with tryptophan, valine, threonine, leucine, isoleucine, cysteine, glutamic acid, lysine, tyrosine, arginine, phenylalanine, glutamine, methionine, proline, aspartic acid, asparagine, histidine, or serine; or (j') the amino acid residue at the position 337 (phenylalanine residue) has been substituted with arginine, glycine, serine, lysine, glutamine, threonine, histidine, alanine, cysteine, or valine; and those obtained by a combination of two or more substations (a') to (j') mentioned above.

The alkaline protease variant of the present invention also includes alkaline protease variants each consisting of an amino acid sequence having an identity of 90% or more with the amino acid sequence represented by SEQ ID NO: 2 in which (a") an amino acid residue at a position corresponding to the position 6 has been substituted with tryptophan, leucine, valine, isoleucine, methionine, tyrosine, glutamine, lysine, threonine, phenylalanine, arginine, serine, cysteine, alanine, or histidine; (b") an amino acid residue at a position corresponding to the position 15 has been substituted with glutamic acid, methionine, aspartic acid, valine, glutamine, arginine, cysteine, tryptophan, alanine, or phenylalanine; (c") an amino acid residue at a position corresponding to the position 16 has been substituted with methionine, glutamic acid, arginine, valine, lysine, phenylalanine, tyrosine, isoleucine, histidine, aspartic acid, or cysteine; (d") an amino acid residue at a position corresponding to the position 65 has been substituted with tryptophan; (e") an amino acid residue at a position corresponding to the position 66 has been substituted with histidine, tryptophan, serine, or leucine; (f") an amino acid residue at a position corresponding to the position 82 has been substituted with alanine, glutamic acid, glutamine, serine, cysteine, glycine, histidine, lysine, arginine, methionine, or asparagine; (g") an amino acid residue at a position corresponding to the position 83 has been substituted with alanine, serine, or cysteine; (h") an amino acid residue at a position corresponding to the position 204 has been substituted with glutamic acid, aspartic acid, cysteine, valine, threonine, proline, histidine, isoleucine, tryptophan, serine, asparagine, lysine, or arginine; (i") an amino acid residue at a position corresponding to the position 319 has been substituted with tryptophan, valine, threonine, leucine, isoleucine, cysteine, glutamic acid, lysine, tyrosine, arginine, phenylalanine, glutamine, methionine, proline, aspartic acid, asparagine, histidine, or serine; or (j") an amino acid residue at a position corresponding to the position 337 has been substituted with arginine, glycine, serine, lysine, glutamine, threonine, histidine, alanine, cysteine, or valine; and those obtained by a combination of two or more substations (a') to (j') mentioned above.

For example, in the alkaline protease variant of the present invention, any one or a plurality of the amino acid residues may be simultaneously substituted at the position 6 or a position corresponding thereto, the position 15 or a position corresponding thereto, the position 16 or a position corresponding thereto, the position 65 or a position corresponding thereto, the position 66 or a position corresponding thereto, the position 82 or a position corresponding thereto, the position 83 or a position corresponding thereto, the position 204 or a position corresponding thereto, the position 319 or a position corresponding thereto, and the position 337 or a position corresponding thereto in the amino acid sequence represented by SEQ ID NO: 2.

Preferably, in the alkaline protease variant of the present invention, the amino acid residue at the position 6 or a position corresponding thereto has been substituted with tryptophan, leucine, valine or isoleucine; the amino acid residue at the position 15 or a position corresponding thereto has been substituted with glutamic acid, methionine aspartic acid or valine; the amino acid residue at the position 16 or a position corresponding thereto has been substituted with methionine, glutamic acid, arginine or valine; the amino acid residue at the position 65 or a position corresponding thereto has been substituted with tryptophan; the amino acid residue at the position 66 or a position corresponding thereto has been substituted with histidine; the amino acid residue at the position 82 or a position corresponding thereto has been substituted with alanine, glutamic acid, glutamine or serine; the amino acid residue at the position 83 or a position corresponding thereto has been substituted with alanine or serine; the amino acid residue at the position 204 or a position corresponding thereto has been substituted with glutamic acid, aspartic acid, or tryptophan; the amino acid residue at the position 319 or a position corresponding thereto has been substituted with tryptophan, valine, threonine, leucine, isoleucine or phenylalanine; and/or the amino acid residue at the 337-position or a position corresponding thereto has been substituted with arginine or valine, in the amino acid sequence represented by SEQ ID NO: 2.

More preferably, in the alkaline protease variant of the present invention, the amino acid residue at the position 6 or a position corresponding thereto has been substituted with tryptophan; the amino acid residue at the position 15 or a position corresponding thereto has been substituted with glutamic acid; the amino acid residue at the position 16 or a position corresponding thereto has been substituted with methionine; the amino acid residue at the position 65 or a position corresponding thereto has been substituted with tryptophan; the amino acid residue at the position 66 or a position corresponding thereto has been substituted with histidine; the amino acid residue at the position 82 or a position corresponding thereto has been substituted with alanine; the amino acid residue at the position 83 or a position corresponding thereto has been substituted with alanine; the amino acid residue at the position 204 or a position corresponding thereto has been substituted with glutamic acid; the amino acid residue at the position 319 or a position corresponding thereto has been substituted with tryptophan; and/or the amino acid residue at the position 337 or a position corresponding thereto has been substituted with arginine, in the amino acid sequence represented by SEQ ID NO: 2.

In the present invention, "the amino acid residue at a corresponding position" can be identified through comparison of amino acid sequences of alkaline proteases by using a known algorithm (e.g., the Lipman-Pearson method), to thereby assign maximum homology to conserved amino acid residues present in the amino acid sequences. When the amino acid sequences of the alkaline proteases are aligned through such a method, no matter what insertion or deletion is present in the amino acid sequences, the positions of the homologous amino acid residues in each of the proteases can be determined. Conceivably, the homologous amino acid residues are located at the same positions in the three-dimensional structures of the alkaline proteases, and thus these proteases are analogous in terms of specificity-related functions.

For example, when the amino acid sequence of SEQ ID NO: 2 is compared with that of protease KP9860 and that of protease KP9865 through the aforementioned method, the following relations can be determined:

(a) the amino acid residue at position 6 (glycine residue) in the amino acid sequence represented by SEQ ID NO: 2 corresponds to the glycine residue at the position 6 of protease KP9860 and to the glycine residue at the position 6 of protease KP9865;

(b) the amino acid residue at position 15 (serine residue) in the amino acid sequence represented by SEQ ID NO: 2 corresponds to the serine residue at the position 15 of protease KP9860 and to the serine residue at the position 15 of protease KP9865;

(c) the amino acid residue at position 16 (serine residue) in the amino acid sequence represented by SEQ ID NO: 2 corresponds to the serine residue at the position 16 of protease KP9860 and to the serine residue at the position 16 of protease KP9865;

(d) the amino acid residue at position 65 (threonine residue) in the amino acid sequence represented by SEQ ID NO: 2 corresponds to the threonine residue at the position 65 of protease KP9860 and to the threonine residue at the position 65 of protease KP9865;

(e) the amino acid residue at position 66 (asparagine residue) in the amino acid sequence represented by SEQ ID NO: 2 corresponds to the asparagine residue at the position 66 of protease KP9860 and to the asparagine residue at the position 66 of protease KP9865;

(f) the amino acid residue at position 82 (threonine residue) in the amino acid sequence represented by SEQ ID NO: 2 corresponds to the threonine residue at the position 82 of protease KP9860 and to the threonine residue at the position 82 of protease KP9865;

(g) the amino acid residue at position 83 (asparagine residue) in the amino acid sequence represented by SEQ ID NO: 2 corresponds to the asparagine residue at the position 83 of protease KP9860 and to the asparagine residue at the position 83 of protease KP9865;

(h) the amino acid residue at position 204 (glutamine residue) in the amino acid sequence represented by SEQ ID NO: 2 corresponds to the glutamine residue at the position 204 of protease KP9860 and to the glutamine residue at the position 204 of protease KP9865;

(i) the amino acid residue at position 319 (alanine residue) in the amino acid sequence represented by SEQ ID NO: 2 corresponds to the alanine residue at the position 319 of protease KP9860 and to the alanine residue at the position 319 of protease KP9865; and (j) the amino acid residue at position 337 (phenylalanine residue) in the amino acid sequence represented by SEQ ID NO: 2 corresponds to the phenylalanine residue at the position 337 of protease KP9860 and to the phenylalanine residue at the position 337 of protease KP9865.

The alkaline protease variant of the present invention may be produced by incorporating a variation at a target position of a protease consisting of an amino acid sequence represented by SEQ ID NO: 2 or an alkaline protease consisting of an amino acid sequence having an identity of 90% or more with the amino acid sequence represented by SEQ ID NO: 2, which is not subjected to modification (hereinafter may be referred to as parent alkaline protease).

The alkaline protease variant of the present invention may be obtained through, for example, the following procedure. Specifically, a cloned gene encoding a parent alkaline protease (e.g., a gene having a nucleotide sequence represented by SEQ ID NO: 1) is subjected to mutation; an appropriate host is transformed with the thus-mutated gene; and the thus-transformed host is subjected to culturing, followed by recovery of the alkaline protease from the cultured product. Cloning of the gene encoding the parent alkaline protease may be performed through a generally employed genetic recombination technique, for example, a method described in WO 99/18218 pamphlet or WO 98/56927 pamphlet.

Mutation of the gene encoding the parent alkaline protease may be performed through any of generally employed site-directed mutagenesis techniques. More specifically, mutation of the gene may be performed by use of, for example, a Site-Directed Mutagenesis System Mutan®-Super Express Km kit (product of Takara Bio Inc.). An arbitrary sequence fragment of the gene may be substituted with a sequence fragment of another gene that corresponds to the arbitrary sequence fragment through recombinant PCR (polymerase chain reaction) method (PCR protocols, Academic Press, New York, 1990).

The method for producing the protease variant of the present invention by use of the above-obtained mutant gene is, for example, as follows: a method in which the mutant gene is ligated into a DNA vector which can consistently amplify the gene, followed by transformation of a host bacterium; or a method in which the mutant gene is introduced into chromosomal DNA of a host bacterium which can consistently maintain the gene. Examples of the host bacterium exhibiting the aforementioned characteristics include bacteria belonging to the genus *Bacillus, Escherichia coli*, mold, yeast, and *Actinomyces*. The protease variant can be produced by inoculating the host microorganisms containing the mutant gene into a culture medium containing an assimilable carbon source, a nitrogen source, and other essential nutrients, followed by culturing through a customary method.

The thus-produced alkaline protease variant of the present invention exhibits oxidizer resistance, maintains casein-degrading activity even in the presence of a fatty acid of high concentration, has a molecular weight of 43,000±2,000 as determined through SDS-PAGE, and exhibits activity within an alkaline pH range and high specific activity. In addition, the alkaline protease variant of the present invention, which maintains high specific activity, is provided with excellent characteristics; i.e., the alkaline protease variant exhibits stability in liquid detergents containing an anionic surfactant such as LAS higher than that of a parent alkaline protease. Therefore, in one aspect of the present invention, there is provided a method for stabilizing an alkaline protease in a liquid detergent, the method including a step of substituting amino acid residue(s). In the method of the present invention, the alkaline protease which is subjected to substitution is the aforementioned parent alkaline protease, and the amino acid residues involved in substitution are those described in the aforementioned (a) to (j).

Therefore, the alkaline protease variant of the present invention is useful as an enzyme to be incorporated into a variety of detergent compositions. In addition, through the stability enhancing method of the present invention, useful enzymes to be incorporated into a variety of detergent compositions can be provided.

No particular limitation is imposed on the amount of the alkaline protease variant of the present invention to be incorporated into a detergent composition, so long as the alkaline protease variant exhibits its activity. The amount of the alkaline protease variant to be incorporated may be 0.1 to 5,000 PU on the basis of 1 kg of the detergent composition, but, from the viewpoint of economy, etc., the incorporation amount is preferably 500 PU or less.

The detergent composition of the present invention may contain, in addition to the alkaline protease variant of the present invention, a variety of enzymes, for example, hydrolase, oxidase, reductase, transferase, lyase, isomerase, ligase, and synthetase. Of these, protease other than the alkaline protease variant of the present invention, cellulase, keratinase, esterase, cutinase, amylase, lipase, pullulanase, pectinase, mannanase, glucosidase, glucanase, cholesterol oxidase, peroxidase, laccase, and the like are preferred, with protease, cellulase, amylase, and lipase being more preferred. Examples of the protease include commercially available products, such as Alcalase®, Esperase®, Savinase®, Everlase®, and Kannase® (Novozymes); Properase® and Purafect® (Genencor); and KAP (Kao Corporation). Examples of the cellulase include Celluzyme® and Carezyme® (Novozymes); and KAC (Kao Corporation), alkaline cellulase produced by *Bacillus* sp. KSM-S237 strain described in JP-A-H10-313859, and mutant alkaline cellulase described in JP-A-2003-313592. Examples of the amylase include Termamyl®, Duramyl®, and Stainzyme® (Novozymes); Purastar® (Genencor), and KAM (Kao Corporation). Examples of the lipase include Lipolase®, Lipolase® Ultra, and Lipex® (Novozymes).

When a protease other than the alkaline protease variant of the present invention is incorporated into a detergent composition in combination with the alkaline protease variant, the protease content is preferably 0.1 to 500 PU on the basis of 1 kg of the detergent composition. When cellulase is incorporated in combination with the alkaline protease variant, the cellulase content is preferably 300 to 3,000,000 KU on the basis of 1 kg of the detergent composition, wherein KU represents a unit as determined by the enzyme activity measuring method described in paragraph [0020] of JP-A-H10-313859.

When amylase is incorporated in combination with the alkaline protease variant, the amylase content is preferably 50 to 500,000 IU on the basis of 1 kg of the detergent composition, wherein IU represents a unit as determined by the amylase activity measuring method described in paragraph of JP-A-H11-43690.

When lipase is incorporated in combination with the alkaline protease variant, the lipase content is preferably 10,000 to 1,000,000 LU on the basis of 1 kg of the detergent composition, wherein LU represents a unit as determined by the lipase activity measuring method described in Example 1 of JP-A-H08-500013.

The detergent composition of the present invention may contain a known detergent component, examples of which include the following.

(1) Surfactant

A surfactant is incorporated into the detergent composition in an amount of 0.5 to 60 mass %, preferably 10 to 45 mass % in the case where the detergent composition is in a powder form, and 20 to 50 mass % in the case where the detergent composition is in a liquid form. When the detergent composition of the present invention is employed as a bleaching agent or a detergent for an automatic dishwasher, the amount of surfactant to be incorporated is generally 1 to 10 mass %, preferably 1 to 5 mass %.

Examples of the surfactant to be employed in the detergent composition of the present invention include one species selected from among an anionic surfactant, a nonionic surfactant, an amphoteric surfactant, and a cationic surfactant; and a combination of these surfactants. Preferably, an anionic surfactant or a nonionic surfactant is employed.

Examples of preferred anionic surfactants include C10-C18 alcohol sulfuric acid ester salts, C8-C20 alkoxy alcohol sulfuric acid ester salts, alkylbenzenesulfonic acid salts, paraffinsulfonic acid salts, α-olefinsulfonic acid salts, α-sulfo fatty acid salts, α-sulfo fatty acid alkyl ester salts, and fatty acid salts. In the present invention, preferred are linear alkylbenzenesulfonic acid salts having an alkyl chain of C10-C14, with being more preferably C12-C14. The counter ionic species is preferably an alkali metal salt or an amine salt, with being more preferably a sodium and/or a potassium; a monoethanolamine; or a diethanolamine.

Examples of preferred nonionic surfactants include polyoxyalkylene C8-C20 alkyl ethers, alkyl polyglycosides, polyoxyalkylene C8-C20 alkylphenyl ethers, polyoxyalkylene sorbitan C8-C22 fatty acid esters, polyoxyalkylene glycol C8-C22 fatty acid esters, and polyoxyethylene-polyoxypropylene block polymers. The nonionic surfactant is preferably a polyoxyalkylene alkyl ether obtained through addition of an alkylene oxide such as ethylene oxide or propylene oxide (4 to 20 mol) to a C10-C18 alcohol, the polyoxyalkylene alkyl ether preferably having an HLB value (calculated by the Griffin method) of 10.5 to 15.0, more preferably 11.0 to 14.5.

(2) Divalent Metal-Ion Trapping Agent

A divalent metal-ion trapping agent is incorporated in an amount of 0.01 to 50 mass %, preferably 5 to 40 mass %. Examples of the divalent metal-ion trapping agent to be employed in the detergent composition of the present invention include condensed phosphoric acid salts such as tripolyphosphoric acid salts, pyrophosphoric acid salts, and orthophosphoric acid salts; aluminosilicates such as zeolite; synthetic layered crystalline silicic acid salts; nitrilotriacetic acid salts; ethylenediaminetetraacetic acid salts; citric acid salts; isocitric acid salts; and polyacetal carboxylic acid salts. Of these, crystalline aluminosilicates (synthetic zeolite) are preferred. Among A-type, X-type, and P-type zeolites, an A-type zeolite is preferred. The preferably employed synthetic zeolite has an average primary particle size of 0.1 to 10 μm, more preferably 0.1 to 5 μm.

(3) Alkaline Agent

An alkaline agent is incorporated in an amount of 0.01 to 80 mass %, preferably 1 to 40 mass %. Examples of the alkaline agent to be employed in a powder detergent include alkali metal carbonates such as sodium carbonate, which is generally called dense ash or light ash, and amorphous alkali metal silicates of JIS No. 1, 2, or 3. These inorganic alkaline agents are effective in forming particle cores upon drying of a detergent to be able to provide a comparatively hard detergent having excellent fluidity. In place of these alkaline agents, for example, sodium sesquicarbonate or sodium hydrogencarbonate may be used, and a phosphoric acid salt such as a tripolyphosphoric acid salt also acts as an alkaline agent. Examples of the alkaline agent which may be employed in a liquid detergent and act as a counter ion to a surfactant include sodium hydroxide and mono-, di-, or triethanolamine, as well as the aforementioned alkaline agents.

(4) Anti-Redeposition Agent

An anti-redeposition agent is incorporated in an amount of 0.001 to 10 mass %, preferably 1 to 5 mass %. Examples of the anti-redeposition agent to be employed in the detergent composition of the present invention include polyethylene glycol, a carboxylic acid polymer, polyvinyl alcohol, and polyvinylpyrrolidone. Of these, a carboxylic acid polymer has metal-ion trapping ability and ability to disperse solid particulate dirt from clothes to a washing bath, as well as anti-redeposition ability. The carboxylic acid polymer is a homopolymer or copolymer formed of acrylic acid, methacrylic acid, itaconic acid, etc., and the copolymer is preferably formed through copolymerization of the aforementioned monomer with maleic acid. The molecular weight of the copolymer is preferably some thousands to 100,000. In addition to the aforementioned carboxylic acid polymer, a polymer such as a polyglycidic acid salt, a cellulose derivative such as carboxymethyl cellulose, or an aminocarboxylic acid polymer such as polyaspartic acid is preferably employed, since these substances also have metal-ion trapping ability, dispersibility, and anti-redeposition ability.

(5) Bleaching Agent

A bleaching agent such as hydrogen peroxide or a percarbonate is preferably incorporated in an amount of 1 to 10 mass %. In the case where a bleaching agent is employed, a bleach-activator such as tetraacetylethylenediamine (TAED) or one described in JP-A-H06-316700 may be incorporated in an amount of 0.01 to 10 mass %.

(6) Fluorescent Agent

Examples of the fluorescent agent to be employed in the detergent composition of the present invention include biphenyl fluorescent agents (e.g., Tinopal® CBS-X) and stilbene fluorescent agents (e.g., DM-type fluorescent dyes). Such a fluorescent agent is preferably incorporated in an amount of 0.001 to 2 mass %.

(7) Other Components

The detergent composition of the present invention may further contain a builder, a softening agent, a reducing agent (e.g., a sulfurous acid salt), a defoaming agent (e.g., silicone), or a perfume, which are known in the laundry detergent field; or other additives.

The detergent composition of the present invention can be produced through a customary method using the above-obtained alkaline protease variant of the present invention in combination with the aforementioned other enzymes and/or the aforementioned known detergent components, if needed. The form of the detergent composition may be appropriately selected in accordance with use thereof, and the detergent may assume the form of, for example, liquid, powder, granule, paste, or solid.

The thus-produced detergent composition of the present invention can be employed as, for example, a laundry detergent, a bleaching agent, a detergent for cleaning hard surfaces, a detergent for drainpipes, a denture-cleaning agent, and a detergent for sterilizing medical instruments.

EXAMPLES

The present invention will next be described in more detail by way of examples.

Example 1

Preparation of KP43 Protease

Next will be described a method of preparing a protease employed in enzyme stability evaluation, taking a wild-type KP43 protease as an example.

A plasmid pHA64 (Japanese Patent No. 349293, having a BamHI site and an XbaI site on the downstream side of the expression promoter) was digested simultaneously with restriction enzymes BamHI and XbaI (Roche), and the product was employed as a vector for gene insertion and gene expression.

A DNA fragment represented by SEQ ID NO: 1 and including a wild-type KP43 protease gene (having BamHI site at the 5'-terminus on the upstream side of the gene, and XbaI site at the 3'-terminus on the downstream side of the gene) was digested simultaneously with restriction enzymes BamHI and XbaI and mixed with the above-prepared insertion and expression vector. The mixture was subjected to ligation by use of Ligation High (product of Toyobo). The ligation product was purified through ethanol precipitation, and *Bacillus* sp. KSM-9865 (FERN BP-10139) serving as a host was transformed with the purified product through electroporation. The product was applied to a skimmed milk-containing alkaline LB agar medium (containing 1% bactotrypton, 0.5% yeast extract, 1% sodium chloride, 1% skimmed milk, 1.5% agar, 0.05% sodium carbonate, and 15 ppm tetracycline). From the colonies appeared in the agar medium several days after, a transformant transfected with a protease gene was selected by confirming the presence of skimmed milk dissolution spots. Plasmid DNA was extracted from the transformant, and correct insertion of the protease gene represented by SEQ ID NO: 1 was confirmed. The thus-obtained plasmid was employed as plasmid pHA64TSA.

A KSM-9865 transformant harboring pHA64TSA was inoculated to a seed medium (6.0% (w/v) polypeptone S, 0.1% yeast extract, 1.0% maltose, 0.02% magnesium sulfate heptahydrate, 0.1% potassium dihydrogenphosphate, 0.3% anhydrous sodium carbonate, 30 ppm tetracycline) (5 mL), and shake-cultured at 30° C. for 16 hours. Subsequently, the seed culture medium was inoculated (1% (v/v)) to a culture medium (8% polypeptone S, 0.3% yeast extract, 10% maltose, 0.04% magnesium sulfate heptahydrate, 0.2% potassium dihydrogenphosphate, 1.5% anhydrous sodium carbonate, 30 ppm tetracycline) (30 mL), and shake-cultured at 30° C. for three days. The culture liquid containing KP43 protease obtained through culturing was centrifuged, and the stability of the recovered supernatant in a liquid detergent was evaluated.

Example 2

Production of KP43 Protease Variants

A method of producing KP43 protease variants will next be described, taking a variant "G6A" as an example. In G6A, the 6-position glycine (G6) in the amino acid sequence (SEQ ID NO: 2) of a wild-type mature KP43 protease region was mutated to alanine.

PCR was performed by use of sufficiently diluted plasmid pHA64TSA as a template, primer KG24S2 (SEQ ID NO: 3, having BamHI site) complementary to the upstream region of the initiation codon, and primer G6_R (SEQ ID NO: 4) complementary to the upstream region adjacent to the G6 codon, to thereby amplify a DNA sequence encoding the N-terminal portion of the KP43 protease. Separately, PCR was performed by use of plasmid pHA64TSA as a template, primer G6A_F (SEQ ID NO: 5), a 5'-terminal portion thereof being complementary to primer G6_R) for substituting the codon of G6 by the codon of alanine, and primer KG11S (SEQ ID NO: 6, having XbaI site) on the downstream side of the termination codon, to thereby amplify a DNA sequence encoding the C-terminal portion of the KP43 protease. Subsequently, the thus-obtained PCR products encoding the N-terminal and C-terminal portions were mixed and the mixture was employed as a template. PCR was performed by use of the primer KG24S2 and primer KG11S, to thereby obtain a PCR product containing the full-length of a KP43 protease variant gene in which the G6 codon had been substituted by the codon of alanine. The PCR product was purified through ethanol precipitation, and the purified product was digested simultaneously with restriction enzymes BamHI and XbaI. The digested product was mixed with the vector for insertion and expression of Example 1, and the mixture was subjected to ligation by use of Ligation High (product of Toyobo). The ligation product was purified through ethanol precipitation, and Bacillus sp. KSM-9865 (FERM BP-10139) serving as a host was transformed with the purified product through electroporation. The product was applied to a skimmed milk-containing alkaline LB agar medium. From the colonies appeared in the agar medium several days after, a transformant transfected with a protease gene was selected by confirming the presence of skimmed milk dissolution spots. Thus, a transformant which produces a KP43 protease variant "G6A" in which G6 was mutated to alanine was produced.

The above procedure was repeated, except that primers represented by SEQ ID NOs. listed in the column "Mutation primer•R" of the following Tables 1 to 10 were used instead of primer G6R, and that primers represented by SEQ ID NOs. listed in the column "Mutation primer•F" of the following Tables 1 to 10 were used instead of primer G6A_F, to thereby produce transformants which produce KP43 protease variants having mutations listed in the column "KP43 protease mutation" of the following Tables 1 to 10. Each of the thus-obtained transformants was cultured through the method described in Example 1, to thereby recover a culture supernatant containing a protease variant of interest. The stability of the protease variant in a liquid detergent was evaluated.

TABLE 1

| KP43 protease mutation | Mutation primer · R | | Mutation primer · F | |
|---|---|---|---|---|
| | Primer | SEQ ID NO | Primer | SEQ ID NO |
| G6A | G6_R | SEQ ID NO: 4 | G6A_F | SEQ ID NO: 5 |
| G6C | G6_R | SEQ ID NO: 4 | G6C_F | SEQ ID NO: 7 |
| G6D | G6_R | SEQ ID NO: 4 | G6D_F | SEQ ID NO: 8 |
| G6E | G6_R | SEQ ID NO: 4 | G6E_F | SEQ ID NO: 9 |
| G6F | G6_R | SEQ ID NO: 4 | G6F_F | SEQ ID NO: 10 |
| G6H | G6_R | SEQ ID NO: 4 | G6H_F | SEQ ID NO: 11 |
| G6I | G6_R | SEQ ID NO: 4 | G6I_F | SEQ ID NO: 12 |
| G6K | G6_R | SEQ ID NO: 4 | G6K_F | SEQ ID NO: 13 |
| G6L | G6_R | SEQ ID NO: 4 | G6L_F | SEQ ID NO: 14 |
| G6M | G6_R | SEQ ID NO: 4 | G6M_F | SEQ ID NO: 15 |
| G6N | G6_R | SEQ ID NO: 4 | G6N_F | SEQ ID NO: 16 |
| G6P | G6_R | SEQ ID NO: 4 | G6P_F | SEQ ID NO: 17 |
| G6Q | G6_R | SEQ ID NO: 4 | G6Q_F | SEQ ID NO: 18 |
| G6R | G6_R | SEQ ID NO: 4 | G6R_F | SEQ ID NO: 19 |
| G6S | G6_R | SEQ ID NO: 4 | G6S_F | SEQ ID NO: 20 |
| G6T | G6_R | SEQ ID NO: 4 | G6T_F | SEQ ID NO: 21 |
| G6V | G6_R | SEQ ID NO: 4 | G6V_F | SEQ ID NO: 22 |
| G6W | G6_R | SEQ ID NO: 4 | G6W_F | SEQ ID NO: 23 |
| G6Y | G6_R | SEQ ID NO: 4 | G6Y_F | SEQ ID NO: 24 |

TABLE 2

| KP43 protease mutation | Mutation primer · R | | Mutation primer · F | |
|---|---|---|---|---|
| | Primer | SEQ ID NO | Primer | SEQ ID NO |
| S15A | S15_R | SEQ ID NO: 25 | S15A_F | SEQ ID NO: 26 |
| S15C | S15_R | SEQ ID NO: 25 | S15C_F | SEQ ID NO: 27 |
| S15D | S15_R | SEQ ID NO: 25 | S15D_F | SEQ ID NO: 28 |
| S15E | S15_R | SEQ ID NO: 25 | S15E_F | SEQ ID NO: 29 |
| S15F | S15_R | SEQ ID NO: 25 | S15F_F | SEQ ID NO: 30 |
| S15G | S15_R | SEQ ID NO: 25 | S15G_F | SEQ ID NO: 31 |
| S15I | S15_R | SEQ ID NO: 25 | S15I_F | SEQ ID NO: 32 |
| S15K | S15_R | SEQ ID NO: 25 | S15K_F | SEQ ID NO: 33 |
| S15L | S15_R | SEQ ID NO: 25 | S15L_F | SEQ ID NO: 34 |
| S15M | S15_R | SEQ ID NO: 25 | S15M_F | SEQ ID NO: 35 |
| S15N | S15_R | SEQ ID NO: 25 | S15N_F | SEQ ID NO: 36 |
| S15P | S15_R | SEQ ID NO: 25 | S15P_F | SEQ ID NO: 37 |
| S15Q | S15_R | SEQ ID NO: 25 | S15Q_F | SEQ ID NO: 38 |
| S15R | S15_R | SEQ ID NO: 25 | S15R_F | SEQ ID NO: 39 |
| S15T | S15_R | SEQ ID NO: 25 | S15T_F | SEQ ID NO: 40 |
| S15V | S15_R | SEQ ID NO: 25 | S15V_F | SEQ ID NO: 41 |
| S15W | S15_R | SEQ ID NO: 25 | S15W_F | SEQ ID NO: 42 |
| S15Y | S15_R | SEQ ID NO: 25 | S15Y_F | SEQ ID NO: 43 |

TABLE 3

| KP43 protease mutation | Mutation primer · R Primer | SEQ ID NO | Mutation primer · F Primer | SEQ ID NO |
|---|---|---|---|---|
| S16A | S16_R | SEQ ID NO: 44 | S16A_F | SEQ ID NO: 45 |
| S16C | S16_R | SEQ ID NO: 44 | S16C_F | SEQ ID NO: 46 |
| S16D | S16_R | SEQ ID NO: 44 | S16D_F | SEQ ID NO: 47 |
| S16E | S16_R | SEQ ID NO: 44 | S16E_F | SEQ ID NO: 48 |
| S16F | S16_R | SEQ ID NO: 44 | S16F_F | SEQ ID NO: 49 |
| S16G | S16_R | SEQ ID NO: 44 | S16G_F | SEQ ID NO: 50 |
| S16H | S16_R | SEQ ID NO: 44 | S16H_F | SEQ ID NO: 51 |
| S16I | S16_R | SEQ ID NO: 44 | S16I_F | SEQ ID NO: 52 |
| S16K | S16_R | SEQ ID NO: 44 | S16K_F | SEQ ID NO: 53 |
| S16L | S16_R | SEQ ID NO: 44 | S16L_F | SEQ ID NO: 54 |
| S16M | S16_R | SEQ ID NO: 44 | S16M_F | SEQ ID NO: 55 |
| S16N | S16_R | SEQ ID NO: 44 | S16N_F | SEQ ID NO: 56 |
| S16P | S16_R | SEQ ID NO: 44 | S16P_F | SEQ ID NO: 57 |
| S16R | S16_R | SEQ ID NO: 44 | S16R_F | SEQ ID NO: 58 |
| S16V | S16_R | SEQ ID NO: 44 | S16V_F | SEQ ID NO: 59 |
| S16W | S16_R | SEQ ID NO: 44 | S16W_F | SEQ ID NO: 60 |
| S16Y | S16_R | SEQ ID NO: 44 | S16Y_F | SEQ ID NO: 61 |

TABLE 4

| KP43 protease mutation | Mutation primer · R Primer | SEQ ID NO | Mutation primer · F Primer | SEQ ID NO |
|---|---|---|---|---|
| T65A | T65_R | SEQ ID NO: 62 | T65A_F | SEQ ID NO: 63 |
| T65C | T65_R | SEQ ID NO: 62 | T65C_F | SEQ ID NO: 64 |
| T65D | T65_R | SEQ ID NO: 62 | T65D_F | SEQ ID NO: 65 |
| T65E | T65_R | SEQ ID NO: 62 | T65E_F | SEQ ID NO: 66 |
| T65F | T65_R | SEQ ID NO: 62 | T65F_F | SEQ ID NO: 67 |
| T65G | T65_R | SEQ ID NO: 62 | T65G_F | SEQ ID NO: 68 |
| T65H | T65_R | SEQ ID NO: 62 | T65H_F | SEQ ID NO: 69 |
| T65I | T65_R | SEQ ID NO: 62 | T65I_F | SEQ ID NO: 70 |
| T65K | T65_R | SEQ ID NO: 62 | T65K_F | SEQ ID NO: 71 |
| T65L | T65_R | SEQ ID NO: 62 | T65L_F | SEQ ID NO: 72 |
| T65M | T65_R | SEQ ID NO: 62 | T65M_F | SEQ ID NO: 73 |
| T65N | T65_R | SEQ ID NO: 62 | T65N_F | SEQ ID NO: 74 |
| T65Q | T65_R | SEQ ID NO: 62 | T65Q_F | SEQ ID NO: 75 |
| T65R | T65_R | SEQ ID NO: 62 | T65R_F | SEQ ID NO: 76 |
| T65S | T65_R | SEQ ID NO: 62 | T65S_F | SEQ ID NO: 77 |
| T65V | T65_R | SEQ ID NO: 62 | T65V_F | SEQ ID NO: 78 |
| T65W | T65_R | SEQ ID NO: 62 | T65W_F | SEQ ID NO: 79 |
| T65Y | T65_R | SEQ ID NO: 62 | T65Y_F | SEQ ID NO: 80 |

TABLE 5

| KP43 protease mutation | Mutation primer · R Primer | SEQ ID NO | Mutation primer · F Primer | SEQ ID NO |
|---|---|---|---|---|
| N66A | N66_R | SEQ ID NO: 81 | N66A_F | SEQ ID NO: 82 |
| N66C | N66_R | SEQ ID NO: 81 | N66C_F | SEQ ID NO: 83 |
| N66D | N66_R | SEQ ID NO: 81 | N66D_F | SEQ ID NO: 84 |
| N66E | N66_R | SEQ ID NO: 81 | N66E_F | SEQ ID NO: 85 |
| N66F | N66_R | SEQ ID NO: 81 | N66F_F | SEQ ID NO: 86 |
| N66G | N66_R | SEQ ID NO: 81 | N66G_F | SEQ ID NO: 87 |
| N66H | N66_R | SEQ ID NO: 81 | N66H_F | SEQ ID NO: 88 |
| N66I | N66_R | SEQ ID NO: 81 | N66I_F | SEQ ID NO: 89 |
| N66K | N66_R | SEQ ID NO: 81 | N66K_F | SEQ ID NO: 90 |
| N66L | N66_R | SEQ ID NO: 81 | N66L_F | SEQ ID NO: 91 |
| N66M | N66_R | SEQ ID NO: 81 | N66M_F | SEQ ID NO: 92 |
| N66P | N66_R | SEQ ID NO: 81 | N66P_F | SEQ ID NO: 93 |
| N66Q | N66_R | SEQ ID NO: 81 | N66Q_F | SEQ ID NO: 94 |
| N66R | N66_R | SEQ ID NO: 81 | N66R_F | SEQ ID NO: 95 |
| N66S | N66_R | SEQ ID NO: 81 | N66S_F | SEQ ID NO: 96 |
| N66T | N66_R | SEQ ID NO: 81 | N66T_F | SEQ ID NO: 97 |
| N66V | N66_R | SEQ ID NO: 81 | N66V_F | SEQ ID NO: 98 |
| N66W | N66_R | SEQ ID NO: 81 | N66W_F | SEQ ID NO: 99 |
| N66Y | N66_R | SEQ ID NO: 81 | N66Y_F | SEQ ID NO: 100 |

TABLE 6

| KP43 protease mutation | Mutation primer · R Primer | SEQ ID NO | Mutation primer · F Primer | SEQ ID NO |
|---|---|---|---|---|
| T82A | T82_R | SEQ ID NO: 101 | T82A_F | SEQ ID NO: 102 |
| T82C | T82_R | SEQ ID NO: 101 | T82C_F | SEQ ID NO: 103 |
| T82D | T82_R | SEQ ID NO: 101 | T82D_F | SEQ ID NO: 104 |
| T82E | T82_R | SEQ ID NO: 101 | T82E_F | SEQ ID NO: 105 |
| T82F | T82_R | SEQ ID NO: 101 | T82F_F | SEQ ID NO: 106 |
| T82G | T82_R | SEQ ID NO: 101 | T82G_F | SEQ ID NO: 107 |
| T82H | T82_R | SEQ ID NO: 101 | T82H_F | SEQ ID NO: 108 |
| T82I | T82_R | SEQ ID NO: 101 | T82I_F | SEQ ID NO: 109 |
| T82K | T82_R | SEQ ID NO: 101 | T82K_F | SEQ ID NO: 110 |
| T82L | T82_R | SEQ ID NO: 101 | T82L_F | SEQ ID NO: 111 |
| T82M | T82_R | SEQ ID NO: 101 | T82M_F | SEQ ID NO: 112 |
| T82N | T82_R | SEQ ID NO: 101 | T82N_F | SEQ ID NO: 113 |
| T82P | T82_R | SEQ ID NO: 101 | T82P_F | SEQ ID NO: 114 |
| T82Q | T82_R | SEQ ID NO: 101 | T82Q_F | SEQ ID NO: 115 |
| T82R | T82_R | SEQ ID NO: 101 | T82R_F | SEQ ID NO: 116 |
| T82S | T82_R | SEQ ID NO: 101 | T82S_F | SEQ ID NO: 117 |
| T82V | T82_R | SEQ ID NO: 101 | T82V_F | SEQ ID NO: 118 |
| T82W | T82_R | SEQ ID NO: 101 | T82W_F | SEQ ID NO: 119 |
| T82Y | T82_R | SEQ ID NO: 101 | T82Y_F | SEQ ID NO: 120 |

TABLE 7

| KP43 protease mutation | Mutation primer · R Primer | SEQ ID NO | Mutation primer · F Primer | SEQ ID NO |
|---|---|---|---|---|
| N83A | N83_R | SEQ ID NO: 121 | N83A_F | SEQ ID NO: 122 |
| N83C | N83_R | SEQ ID NO: 121 | N83C_F | SEQ ID NO: 123 |
| N83D | N83_R | SEQ ID NO: 121 | N83D_F | SEQ ID NO: 124 |
| N83E | N83_R | SEQ ID NO: 121 | N83E_F | SEQ ID NO: 125 |
| N83F | N83_R | SEQ ID NO: 121 | N83F_F | SEQ ID NO: 126 |
| N83G | N83_R | SEQ ID NO: 121 | N83G_F | SEQ ID NO: 127 |
| N83H | N83_R | SEQ ID NO: 121 | N83H_F | SEQ ID NO: 128 |
| N83I | N83_R | SEQ ID NO: 121 | N83I_F | SEQ ID NO: 129 |
| N83K | N83_R | SEQ ID NO: 121 | N83K_F | SEQ ID NO: 130 |
| N83L | N83_R | SEQ ID NO: 121 | N83L_F | SEQ ID NO: 131 |
| N83M | N83_R | SEQ ID NO: 121 | N83M_F | SEQ ID NO: 132 |
| N83P | N83_R | SEQ ID NO: 121 | N83P_F | SEQ ID NO: 133 |
| N83Q | N83_R | SEQ ID NO: 121 | N83Q_F | SEQ ID NO: 134 |
| N83R | N83_R | SEQ ID NO: 121 | N83R_F | SEQ ID NO: 135 |
| N83S | N83_R | SEQ ID NO: 121 | N83S_F | SEQ ID NO: 136 |
| N83T | N83_R | SEQ ID NO: 121 | N83T_F | SEQ ID NO: 137 |
| N83V | N83_R | SEQ ID NO: 121 | N83V_F | SEQ ID NO: 138 |
| N83W | N83_R | SEQ ID NO: 121 | N83W_F | SEQ ID NO: 139 |
| N83Y | N83_R | SEQ ID NO: 121 | N83Y_F | SEQ ID NO: 140 |

TABLE 8

| KP43 protease mutation | Mutation primer · R Primer | SEQ ID NO | Mutation primer · F Primer | SEQ ID NO |
|---|---|---|---|---|
| Q204A | Q204_R | SEQ ID NO: 141 | Q204A_F | SEQ ID NO: 142 |
| Q204C | Q204_R | SEQ ID NO: 141 | Q204C_F | SEQ ID NO: 143 |
| Q204D | Q204_R | SEQ ID NO: 141 | Q204D_F | SEQ ID NO: 144 |
| Q204E | Q204_R | SEQ ID NO: 141 | Q204E_F | SEQ ID NO: 145 |
| Q204F | Q204_R | SEQ ID NO: 141 | Q204F_F | SEQ ID NO: 146 |
| Q204G | Q204_R | SEQ ID NO: 141 | Q204G_F | SEQ ID NO: 147 |
| Q204H | Q204_R | SEQ ID NO: 141 | Q204H_F | SEQ ID NO: 148 |
| Q204I | Q204_R | SEQ ID NO: 141 | Q204I_F | SEQ ID NO: 149 |
| Q204K | Q204_R | SEQ ID NO: 141 | Q204K_F | SEQ ID NO: 150 |
| Q204L | Q204_R | SEQ ID NO: 141 | Q204L_F | SEQ ID NO: 151 |
| Q204M | Q204_R | SEQ ID NO: 141 | Q204M_F | SEQ ID NO: 152 |
| Q204N | Q204_R | SEQ ID NO: 141 | Q204N_F | SEQ ID NO: 153 |
| Q204P | Q204_R | SEQ ID NO: 141 | Q204P_F | SEQ ID NO: 154 |
| Q204R | Q204_R | SEQ ID NO: 141 | Q204R_F | SEQ ID NO: 155 |
| Q204S | Q204_R | SEQ ID NO: 141 | Q204S_F | SEQ ID NO: 156 |
| Q204T | Q204_R | SEQ ID NO: 141 | Q204T_F | SEQ ID NO: 157 |

TABLE 8-continued

| KP43 protease | Mutation primer · R | | Mutation primer · F | |
|---|---|---|---|---|
| mutation | Primer | SEQ ID NO | Primer | SEQ ID NO |
| Q204V | Q204_R | SEQ ID NO: 141 | Q204V_F | SEQ ID NO: 158 |
| Q204W | Q204_R | SEQ ID NO: 141 | Q204W_F | SEQ ID NO: 159 |
| Q204Y | Q204_R | SEQ ID NO: 141 | Q204Y_F | SEQ ID NO: 160 |

TABLE 9

| KP43 protease | Mutation primer · R | | Mutation primer · F | |
|---|---|---|---|---|
| mutation | Primer | SEQ ID NO | Primer | SEQ ID NO |
| A319C | A319_R | SEQ ID NO: 161 | A319C_F | SEQ ID NO: 162 |
| A319D | A319_R | SEQ ID NO: 161 | A319D_F | SEQ ID NO: 163 |
| A319E | A319_R | SEQ ID NO: 161 | A319E_F | SEQ ID NO: 164 |
| A319F | A319_R | SEQ ID NO: 161 | A319F_F | SEQ ID NO: 165 |
| A319G | A319_R | SEQ ID NO: 161 | A319G_F | SEQ ID NO: 166 |
| A319H | A319_R | SEQ ID NO: 161 | A319H_F | SEQ ID NO: 167 |
| A319I | A319_R | SEQ ID NO: 161 | A319I_F | SEQ ID NO: 168 |
| A319K | A319_R | SEQ ID NO: 161 | A319K_F | SEQ ID NO: 169 |
| A319L | A319_R | SEQ ID NO: 161 | A319L_F | SEQ ID NO: 170 |
| A319M | A319_R | SEQ ID NO: 161 | A319M_F | SEQ ID NO: 171 |
| A319N | A319_R | SEQ ID NO: 161 | A319N_F | SEQ ID NO: 172 |
| A319P | A319_R | SEQ ID NO: 161 | A319P_F | SEQ ID NO: 173 |
| A319Q | A319_R | SEQ ID NO: 161 | A319Q_F | SEQ ID NO: 174 |
| A319R | A319_R | SEQ ID NO: 161 | A319R_F | SEQ ID NO: 175 |
| A319S | A319_R | SEQ ID NO: 161 | A319S_F | SEQ ID NO: 176 |
| A319T | A319_R | SEQ ID NO: 161 | A319T_F | SEQ ID NO: 177 |
| A319V | A319_R | SEQ ID NO: 161 | A319V_F | SEQ ID NO: 178 |
| A319W | A319_R | SEQ ID NO: 161 | A319W_F | SEQ ID NO: 179 |
| A319Y | A319_R | SEQ ID NO: 161 | A319Y_F | SEQ ID NO: 180 |

TABLE 10

| KP43 protease | Mutation primer · R | | Mutation primer · F | |
|---|---|---|---|---|
| mutation | Primer | SEQ ID NO | Primer | SEQ ID NO |
| F337A | F337_R | SEQ ID NO: 181 | F337A_F | SEQ ID NO: 182 |
| F337C | F337_R | SEQ ID NO: 181 | F337C_F | SEQ ID NO: 183 |
| F337D | F337_R | SEQ ID NO: 181 | F337D_F | SEQ ID NO: 184 |
| F337E | F337_R | SEQ ID NO: 181 | F337E_F | SEQ ID NO: 185 |
| F337G | F337_R | SEQ ID NO: 181 | F337G_F | SEQ ID NO: 186 |
| F337H | F337_R | SEQ ID NO: 181 | F337H_F | SEQ ID NO: 187 |
| F337I | F337_R | SEQ ID NO: 181 | F337I_F | SEQ ID NO: 188 |
| F337K | F337_R | SEQ ID NO: 181 | F337K_F | SEQ ID NO: 189 |
| F337L | F337_R | SEQ ID NO: 181 | F337L_F | SEQ ID NO: 190 |
| F337M | F337_R | SEQ ID NO: 181 | F337M_F | SEQ ID NO: 191 |
| F337N | F337_R | SEQ ID NO: 181 | F337N_F | SEQ ID NO: 192 |
| F337P | F337_R | SEQ ID NO: 181 | F337P_F | SEQ ID NO: 193 |
| F337Q | F337_R | SEQ ID NO: 181 | F337Q_F | SEQ ID NO: 194 |
| F337R | F337_R | SEQ ID NO: 181 | F337R_F | SEQ ID NO: 195 |
| F337S | F337_R | SEQ ID NO: 181 | F337S_F | SEQ ID NO: 196 |
| F337T | F337_R | SEQ ID NO: 181 | F337T_F | SEQ ID NO: 197 |
| F337V | F337_R | SEQ ID NO: 181 | F337V_F | SEQ ID NO: 198 |
| F337W | F337_R | SEQ ID NO: 181 | F337W_F | SEQ ID NO: 199 |
| F337Y | F337_R | SEQ ID NO: 181 | F337Y_F | SEQ ID NO: 200 |

Example 3

Method for Determining Protease Activity

Protease activity was determined in the following manner. Specifically, 40 mM Glt-Ala-Ala-Pro-Leu-pNA.$H_2O$ (AAPL) (product of Peptide Laboratory) dissolved in dimethyl sulfoxide (3 parts by volume), 200 mM borate buffer (pH: 10.5) (10 parts by volume), and ion-exchange water (7 parts by volume) were mixed, to thereby prepare a substrate solution. The substrate solution was dispensed in a 96-well assay plate (50 μL/well). Each protease-containing solution was diluted with ion-exchange water to an appropriate concentration, and the diluted protease was added to the assay plate (50 μL/well), whereby reaction was initiated. Immediately after start of reaction, the plate was placed into a chamber (VersaMax™, product of Molecular Device) maintained at 30° C. The change in absorbance at 420 nm was monitored in the kinetic mode for 10 minutes. The measurements were processed by analysis software (Softmax®Pro, product of Molecular Device), and the output of absorbance change rate (mOD/min) was employed as a provisional activity value of the protease.

Example 4

Evaluation of Stability of Variants

Composition A (8% Softanol®, 70H, 14% Emulgen®, 120, 8% acid precursor for linear sodium alkylbenzenesulfonate liquid (LAS-S), 4% Lunac® L-55, 2% ethanol, 4% butoxydiglycol, 3.5% monoethanolamine, 0.1% sodium sulfite, 0.55% citric acid, pH: 9.0) was added to a 96-well plate (90 μL/well). Then, a culture supernatant containing a wild-type KP43 protease or each of the KP43 protease variants was added to a 96-well plate (10 μL/well), followed by sufficient stirring. Immediately after stirring, a portion (10 μL) of the liquid mixture was collected and diluted with ion-exchange water (250 μL), followed by sufficient stirring. The dilution was performed to a dilution factor of 26 folds. The thus-obtained diluted liquid was added to the 96-well assay plate (50 μL/well) to which a substrate solution had been added (50 μL/well). The plate was placed into a microplate-reader (VersaMax™, product of Molecular Device) and the protease activity of the sample was determined. The initial activity value was determined for evaluation of storage stability of the sample. The 96-well assay plate to which each evaluation liquid (composition A and culture supernatant) had been added was maintained in a sealed container at 40° C. After storage for 72 hours, the plate was removed from the container, and the residual activity was determined through the same procedure as employed for the determination of the initial activity. The residual activity (relative value) of each KP43 protease variant was calculated, with respect to the residual activity of the wild-type KP43 protease as 1000.

Figure 2:
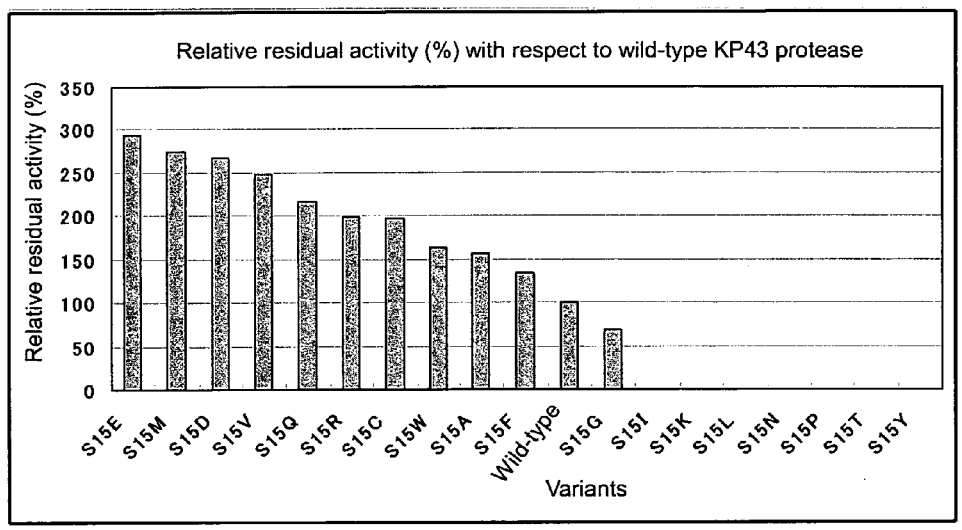
FIG. 2 A graph showing relative residual activities of variants in which the amino acid residue at the position 15 has been substituted.
Figure 3:
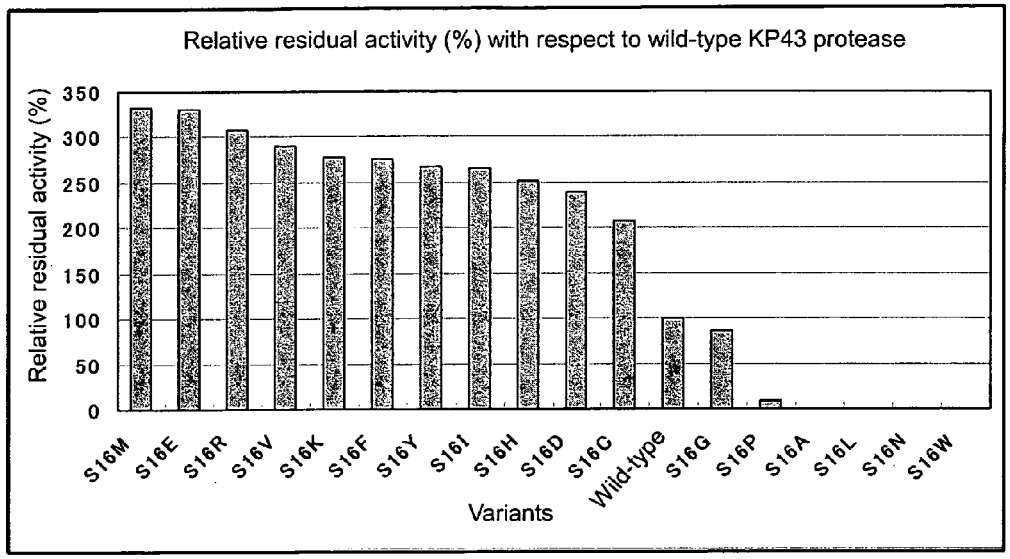
FIG. 3 A graph showing relative residual activities of variants in which the amino acid residue at the position 16 has been substituted.
Figure 4:
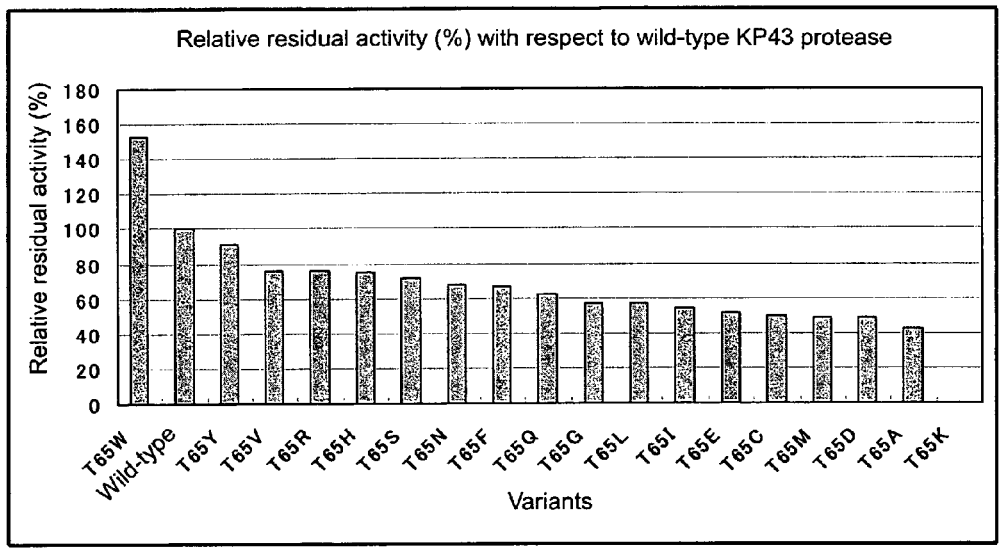
FIG. 4 A graph showing relative residual activities of variants in which the amino acid residue at the position 65 has been substituted.
Figure 5:
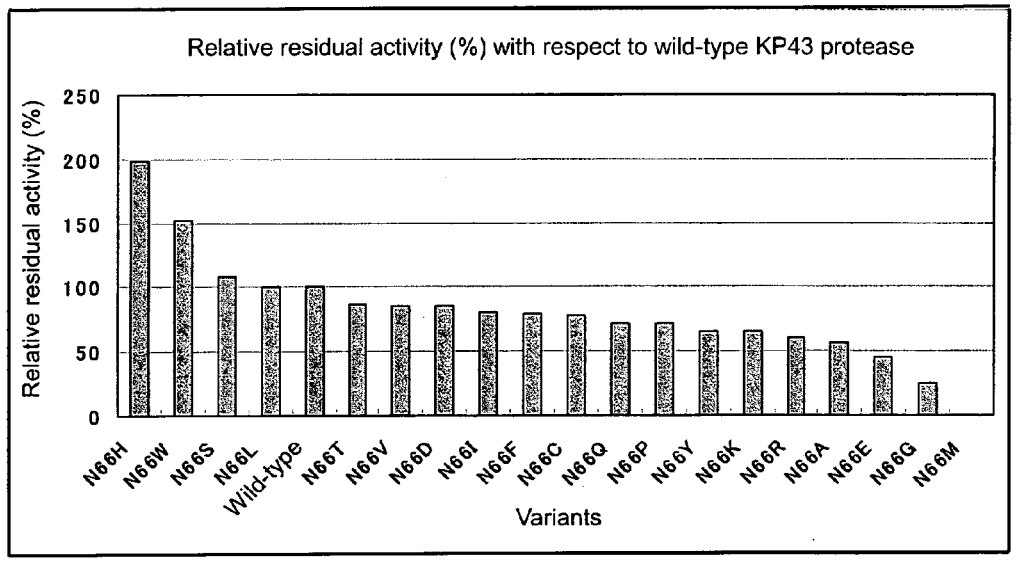
FIG. 5 A graph showing relative residual activities of variants in which the amino acid residue at the position 66 has been substituted.
Figure 6:
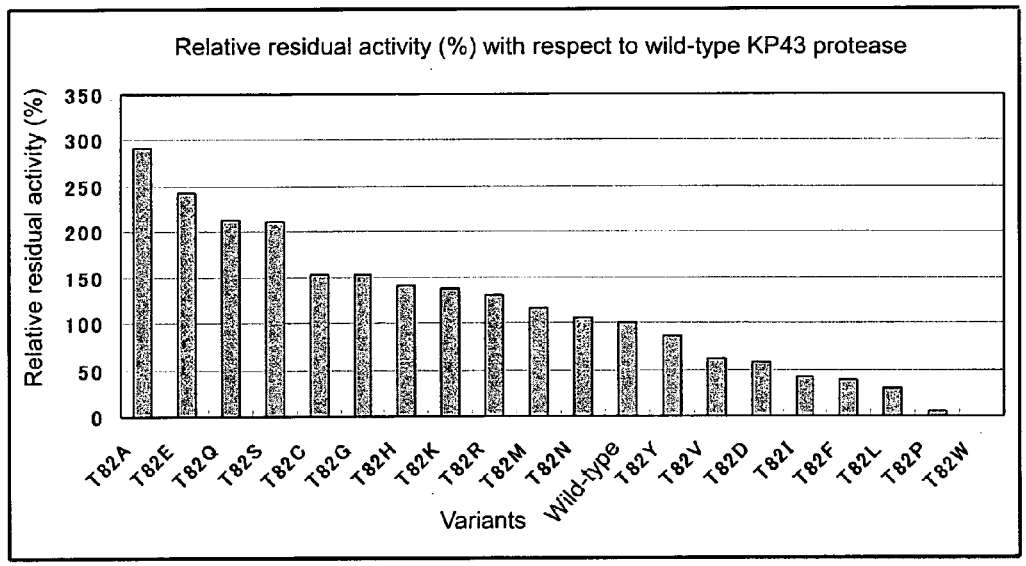
FIG. 6 A graph showing relative residual activities of variants in which the amino acid residue at the position 82 has been substituted.
Figure 7:
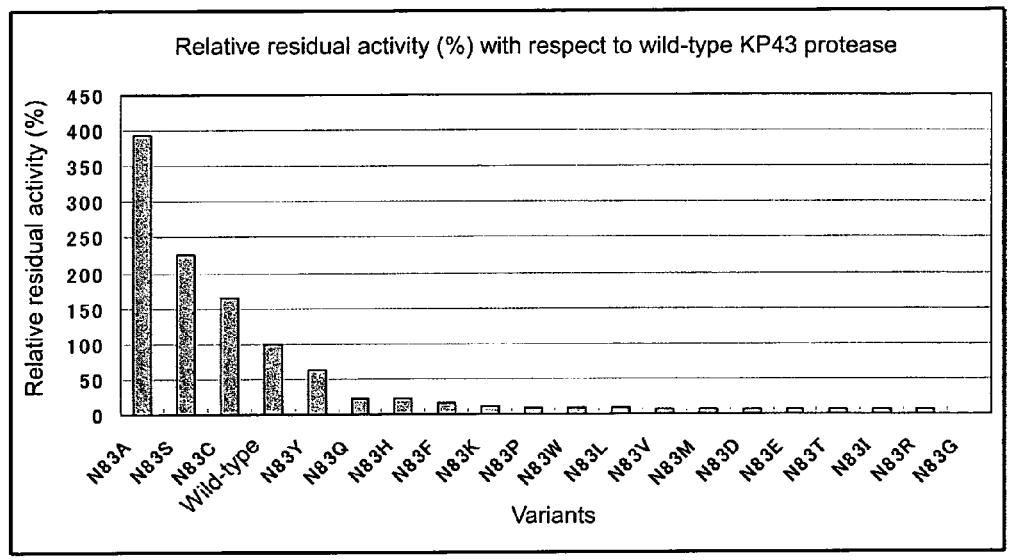
FIG. 7 A graph showing relative residual activities of variants in which the amino acid residue at the position 83 has been substituted.
Figure 8:
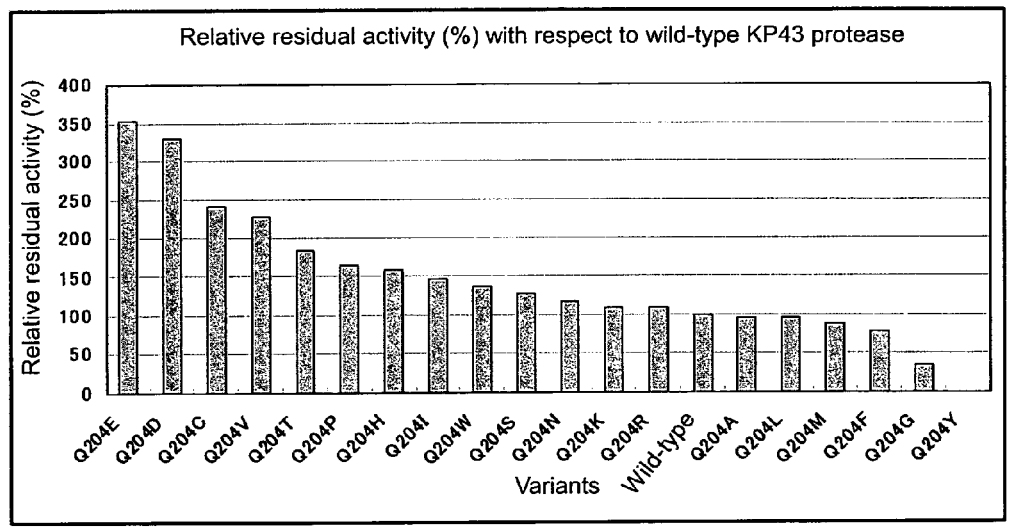
FIG. 8 A graph showing relative residual activities of variants in which the amino acid residue at the position 204 has been substituted.
Figure 9:
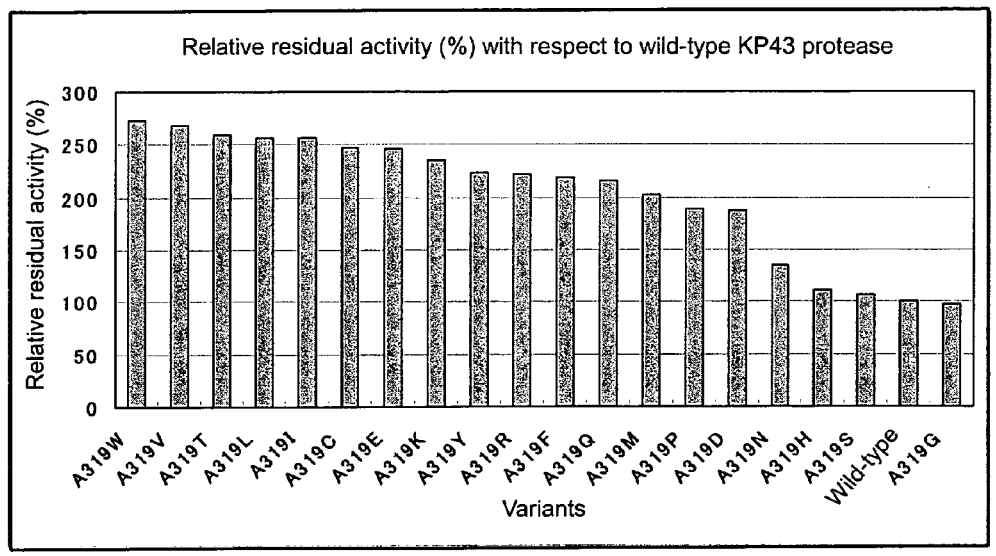
FIG. 9 A graph showing relative residual activities of variants in which the amino acid residue at the position 319 has been substituted.
Figure 10:
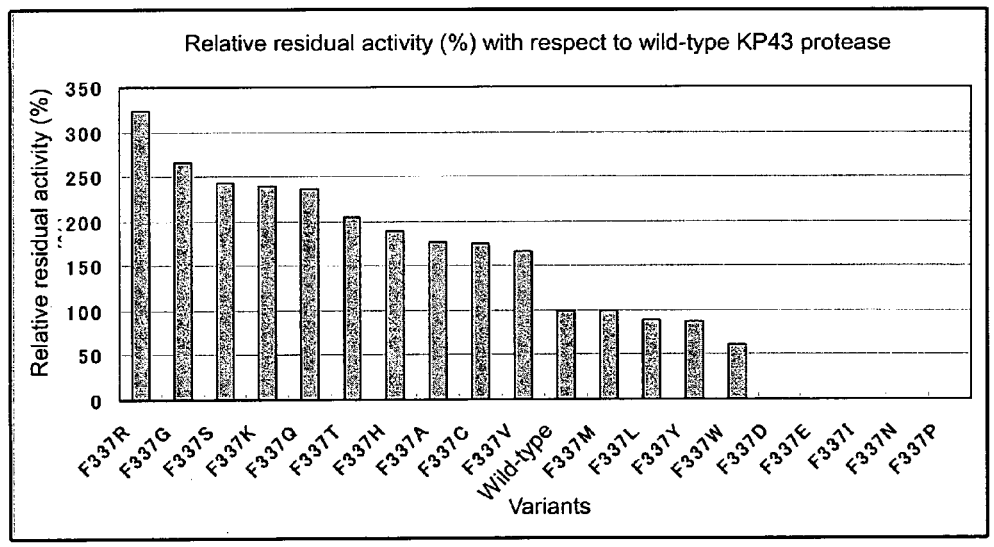
FIG. 10 A graph showing relative residual activities of variants in which the amino acid residue at the position 337 has been substituted.

FIGS. 1 to 10 show the stabilities of wild-type protease and KP43 protease variants.

The invention claimed is:

1. A recombinant protein comprising (a) an amino acid sequence consisting of SEQ ID NO: 2 or (b) an amino acid sequence having 95% or more identity with SEQ ID NO: 2, in which, in both (a) and (b), glutamine at SEQ ID NO: 2 position 204 or at a position corresponding thereto is substituted with: glutamic acid, aspartic acid, cysteine, valine, threonine, proline, histidine, isoleucine, tryptophan, serine, asparagine, lysine or arginine, and wherein the amino acid sequence has alkaline protease activity to cleave the substrate Glt-Ala-Ala-Pro-Leu-pNA to release p-nitroaniline.

2. The recombinant protein according to claim 1, wherein said protein comprises said (a), an amino acid sequence consisting of the amino acid sequence of SEQ ID NO:2 in which glutamine at SEQ ID NO: 2 position 204 is substituted with: glutamic acid, aspartic acid, cysteine, valine, threonine, proline, histidine, isoleucine, tryptophan, serine, asparagine, lysine or arginine.

3. A detergent composition comprising a protein comprising (a) an amino acid sequence consisting of SEQ ID NO: 2 or (b) an amino acid sequence having 95% or more identity with SEQ ID NO: 2, in which, in both (a) and (b), glutamine at SEQ ID NO: 2 position 204 or at the position corresponding thereto is substituted with: glutamic acid, aspartic acid, cysteine, valine, threonine, proline, histidine, isoleucine, tryptophan, serine, asparagine, lysine or arginine, and wherein the amino acid sequence has alkaline protease activity to cleave the substrate Glt-Ala-Ala-Pro-Leu-pNA to release p-nitroaniline.

4. The detergent composition according to claim 3, which comprises an anionic surfactant.

5. A recombinant protein comprising an amino acid sequence consisting of an amino acid sequence having 95% or more identity with the amino acid sequence of SEQ ID NO: 2, and in which the amino acid at SEQ ID NO: 2 position 204, or at the position corresponding thereto, is aspartic acid, and wherein the amino acid sequence has alkaline protease activity to cleave the substrate Glt-Ala-Ala-Pro-Leu-pNA to release p-nitroaniline.

6. The recombinant protein of claim 5, wherein the identity is 96% or more.

7. The recombinant protein of claim 6, wherein the identity is 97% or more.

8. The recombinant protein of claim 7, wherein the identity is 98% or more.

9. The recombinant protein of claim 8, wherein the identity is 99% or more.

10. Culture medium from the culture of an isolated transformed host cell that contains a recombinant protein produced by the host cell, wherein the amino acid sequence of the recombinant protein comprises an amino acid sequence consisting of a sequence having 95% or more identity with SEQ ID NO: 2, and in which the amino acid at SEQ ID NO: 2 position 204, or the position corresponding thereto, is aspartic acid, and wherein the amino acid sequence has alkaline protease activity to cleave the substrate Glt-Ala-Ala-Pro-Leu-pNA to release p-nitroaniline.

11. The culture medium of claim 10, wherein the identity is 96% or more.

12. The culture medium of claim 11, wherein the identity is 97% or more.

13. The culture medium of claim 12, wherein the identity is 98% or more.

14. The culture medium of claim 13, wherein the identity is 99% or more.

15. The recombinant alkaline protease according to claim 1, wherein one or more of SEQ ID NO: 2 positions selected from positions 6, 65, 66, 82, 83, 319 and 337, or positions corresponding thereto, are also substituted.

16. A detergent composition comprising the recombinant protein of claim 5.

* * * * *